United States Patent
Sun et al.

(10) Patent No.: US 10,000,506 B2
(45) Date of Patent: Jun. 19, 2018

(54) OPTICALLY ACTIVE 2-HYDROXY TETRAHYDROTHIENOPYRIDINE DERIVATIVES, PREPARATION METHOD AND USE IN MANUFACTURE OF MEDICAMENT THEREOF

(71) Applicant: Jiangsu Vcare PharmaTech Co., Ltd., Nanjing, Jiangsu Province (CN)

(72) Inventors: Hong-Bin Sun, Nanjing (CN); Jiaqi Shan, Nanjing (CN); Boyu Zhang, Nanjing (CN); Fang Yuan, Nanjing (CN)

(73) Assignee: Jiangsu Vcare PharmaTech Co., Ltd., Nanjing (CN)

(*) Notice: Subject to any disclaimer, the term of this patent is extended or adjusted under 35 U.S.C. 154(b) by 0 days. days.

(21) Appl. No.: 15/275,967

(22) Filed: Sep. 26, 2016

(65) Prior Publication Data

US 2017/0121341 A1 May 4, 2017

Related U.S. Application Data

(63) Continuation of application No. 14/322,939, filed on Jul. 3, 2014, which is a continuation of application
(Continued)

(30) Foreign Application Priority Data

Feb. 2, 2010 (CN) .......................... 2010 1 0104091
Dec. 30, 2010 (CN) .......................... 2010 1 0624329

(51) Int. Cl.
*C07D 515/02* (2006.01)
*C07D 513/02* (2006.01)
(Continued)

(52) U.S. Cl.
CPC ........ *C07D 495/04* (2013.01); *A61K 31/4365* (2013.01); *C07B 2200/07* (2013.01)

(58) Field of Classification Search
CPC .................................................. C07D 495/04
(Continued)

(56) References Cited

U.S. PATENT DOCUMENTS 4,740,510 A * 4/1988 Badorc ................ C07D 495/04
514/233.8
4,847,265 A 7/1989 Badorc et al.
(Continued)

FOREIGN PATENT DOCUMENTS

CN 101591344 * 12/2009
CN 101591344 A 12/2009
(Continued)

OTHER PUBLICATIONS

Pereillo; Drug Metabolism and Disposition 2002, 30, 1288-1295.*
(Continued)

*Primary Examiner* — Daniel R Carcanague
(74) *Attorney, Agent, or Firm* — McCarter & English, LLP; Steven G. Davis; Wei Song

(57) ABSTRACT

Optically active 2-hydroxytetrahydrothienopyridine derivatives represented by Formula I and pharmaceutically acceptable salts, preparation method and use in the manufacture of a medicament thereof are disclosed. The pharmacodynamic experiment results show that the present compounds of Formula I are useful for inhibiting platelet aggregation. The pharmacokinetic experiment results show that the present compound of Formula I can be converted in vivo into pharmacologically active metabolites and are therefore useful for inhibiting platelet aggregation. Therefore, the present
(Continued)

compounds are useful for the manufacture of a medicament for preventing or treating thrombosis and embolism related diseases.

9 Claims, 4 Drawing Sheets

Related U.S. Application Data

No. 13/576,534, filed as application No. PCT/CN2011/000138 on Jan. 28, 2011, now Pat. No. 8,772,489.

(51) Int. Cl.
| | | |
|---|---|---|
| C07D 221/02 | (2006.01) | |
| A61K 31/44 | (2006.01) | |
| A61K 31/38 | (2006.01) | |
| C07D 409/00 | (2006.01) | |
| A01N 43/42 | (2006.01) | |
| C07D 495/04 | (2006.01) | |
| A61K 31/4365 | (2006.01) | |

(58) Field of Classification Search
USPC .......................................................... 546/114
See application file for complete search history.

(56) References Cited

U.S. PATENT DOCUMENTS

| | | | | |
|---|---|---|---|---|
| 5,190,938 A * | 3/1993 | Badorc | ............... | C07D 491/04 514/301 |
| 5,288,726 A * | 2/1994 | Koike | .................. | C07D 471/04 546/114 |
| 5,436,242 A | 7/1995 | Koike et al. | | |
| 5,874,581 A * | 2/1999 | Ataka | ................... | C07F 7/1856 546/114 |
| 6,573,381 B1 * | 6/2003 | Bousquet | .............. | C07C 309/66 112/113 |
| 8,541,422 B2 | 9/2013 | Kumar et al. | | |
| 8,772,489 B2 | 7/2014 | Sun | | |
| 2014/0018331 A1 | 1/2014 | Kumar et al. | | |

FOREIGN PATENT DOCUMENTS

| | | | |
|---|---|---|---|
| CN | 101845050 | * | 9/2010 |
| CN | 101885730 | * | 11/2010 |
| CN | 101885730 A | | 11/2010 |
| CN | 102212068 A | | 10/2011 |
| CN | 102212069 A | | 10/2011 |
| EP | 0421861 A1 | | 4/1991 |
| EP | 0785205 A1 | | 7/1997 |
| JP | 2001519353 A | | 10/2001 |
| WO | 97/49397 A1 | | 12/1997 |
| WO | WO9749397 | * | 12/1997 |
| WO | 2012/025942 A1 | | 3/2012 |
| WO | WO2012025942 | * | 3/2012 |
| WO | WO2014040498 | * | 3/2014 |

OTHER PUBLICATIONS

Shan; J. Med. Chem. 2012, 55, 3342-3352.*
"Isolation of Optical Isomers", a series of "Kikan kagaku sosetsu (Quarterly Chemical Review)", Japan, 1999, No. 6, p. 8-9.
Burgos etal., "ortho-Metalation/Chlorination of Benzoic Acid Derivatives: Preparation of [benzene-U-13C]-rac-Clopidogrel ([benzene-U-13C]-rac-SR25990C)", Journal of Labelled Compounds and Radiopharmaceuticals, vol. 43, pp. 891-898 (2000).
Dangas, George, et al., "Role of Clopidogrel Loading Dose in Patients with ST-Segment Elevation Myocardial Infarction Undergoing Primary Angioplasty", Journal of teh American College of Cardiology, 54(15):1438-46, 2009.
EFFIENT (prasugrel), Drug Label, 2009.
Gurbel, Paul A., et al., "Clopidogrel for Coronary Stenting, Response Variability, Drug Resistance, and the Effect of Pretreatment Platelet Reactivity", Circulation, 107:2908-2913, 2003.
Gurbel, Paul A., et al., "Combination Antithrombotic Therapies", Circulation, 121:569-583, 2010.
Gurbel, Paul A., et al., "The Relation of Dosing to Clopidogrel Responsiveness and the Incidence of High Post-Treatment Platelet Aggregation in Patients Undergoing Coronary Stenting", Journal of the American College of Cardiology, 45(9):1392-6, 2005.
Hagihara et al., "Comparison of Human Cytochrome P450 Inhibition by the Thienopyridines Prasugrel, Clopidogrel, and Ticlopidine", Drug Metab. Pharmacokinet, vol. 23, No. 6, pp. 412-420 (2008).
Herbert et al., Clopidogrel, A Novel Antiplatelet and Antithrombotic Agent; Cardiovascular Drug Reviews, 1993, vol. 11, No. 2, p. 180-198.
International Search Report for related PCT Application No. PCT/CN2011/000138; dated May 5, 2011, 5pp.
Kazul, Miho, et al., "Identification of the Human Cytochrome P450 Enzymes Involved in the Two Oxidative Steps in the Bioactivation of Clopidogrel to its Pharmacologically Active Metabolite", Drug Metabolism and Disposition, 38(1):92-99, 2010.
Kuliczkowski et al., "Interindividual variability in the response to oral antiplatelet drugs: a position paper of the Working Group on antiplatelet drugs resistance appointed by the Section of Cardiovascular Interventions of the Polish Cardiac Society, endorsed by the Working Group on Thrombosis of the European Society of Cardiology" European Heart Journal (2009) 30, 426-435.
Kumar, Ashok, et al., "Decision on Motions", Patent Interference 106,029 (JTM), Sep. 9, 2016.
Lancet, A randomised, blinded, trial of clopidogrel versus aspirin in patients at risk of ischemis events (CAPRIE): vol. 348; Nov. 16, 1996, p. 1329-1339.
Lau et al., Contribution of Hepatic Cytochrome P450 3A4 Metabolic Activity to the Phenomenon of Clopidogrel Resistance; Circulation, Journal of the American Heart Association; 2004, 109: 166-171.
Lewis et al. "The functional G143E variant of carboxylesterase 1 is associated with increased clopidogrel active metabolite levels and greater clopidogrel response" Pharmacogenet Genomics. Jan. 2013; 23(1): 1-8.
Lins, Robert, et al., "Pharmacokinetic Profile of C0Labled Clopidogrel", Seminars in Thrombosis and Hemostasis, 25(2):29-33, 1999.
Prasugrel, https://en.wikipedia.org/wiki/Prasugrel, downloaded Dec. 12, 2017.
Sangkuhl, Katrin, et al., "Clopidogrel Pathway", Pharmacogenetics and Genomics, 20(7):463-465, 2010.
Savi, et al., Identification and Biological Activity of the Active Metabolite of Clopidogrel: Thromb Haemost, 2000, 84: 891-896.
Savi, P., et al., "Importance of Hepatic Metabolism in the Antiaggregating Activity of the Thienopyridine Clopidogrel", Biochemical Pharmacology, 44(3):527-532, 1992.
Savi, P., et al., "The Antiaggregating Activity of Clopidogrel is due to a Metabolic Activation by the Hepatic Cytochrome P450-1A", Thrombosis and Haemostatis, F.K. Schattauer Verlagsgesellschaft mbH (Stuttgart), 72(2):313-7, 1994.
Sun, Hongbin, et al., "Redeclaration-Bd.R. 203(c)", Patent Interference 106,063(JTM), Oct. 20, 2016.
Tang, et al., Antiplatelet Agent Aspirin and Clopidigrel are Hydrolyzed by Distinct Carboxylesterases, and Clopidogrel is Transesterified in the Presence of Ethyl Alcohol; Journal of Pharmacology and Experimental Therapeutics; JPET, 2006, 319:1467-1476.
Wermuth; "Practice of Medicinal Chemistry" 3rd Ed. 2008, Elsevier, Chapter 26, pp. 533-548.
Wiviott, et al., Prasugrel in patients with Acute Coronary Syndromes, The New England Journal of Medicine, Nov. 15, 2007, vol. 357, No. 20: 2001-2015.

* cited by examiner

OPTICALLY ACTIVE 2-HYDROXY TETRAHYDROTHIENOPYRIDINE DERIVATIVES, PREPARATION METHOD AND USE IN MANUFACTURE OF MEDICAMENT THEREOF

CROSS-REFERENCE TO RELATED APPLICATION

This application is a continuation application of U.S. application Ser. No. 14/322,939, filed Jul. 3, 2014, which is a continuation application of U.S. application Ser. No. 13/576,534 now U.S. Pat. No. 8,772,489, which is 35 U.S.C. § 371 national stage filing of International Application No. PCT/CN2011/000138, filed Jan. 28, 2011, which, in turn, claims the priority of Chinese Patent Application No. 201010104091.5, filed on Feb. 2, 2010 and entitled 2-HYDROXY THIENOPYRIDINE DERIVATIVES, PREPARATION METHOD AND MEDICAL USE THEREOF, and Chinese Patent Application No. 201010624329.7, filed on Dec. 30, 2010, and entitled OPTICALLY ACTIVE 2-HYDROXYTETRAHYDROTHIENOPYRIDINE DERIVATIVES, PREPARATION METHOD AND USE IN MANUFACTURE OF MEDICAMENT THEREOF.

BACKGROUND OF THE INVENTION

1. Field of the Invention

The present invention relates to the field of pharmacochemistry, and more particularly to optically active 2-hydroxytetrahydrothienopyridine derivatives, preparation method and use thereof in the manufacture of a medicament, especially for preventing or treating thrombosis and embolism related diseases.

2. Description of the Related Art

Clopidogrel is an anti-platelet aggregation agent that is most widely used all over the world at present, and used for treating atherosclerosis, acute coronary syndrome (ACS), thrombotic complications, and other diseases in clinic. Clinical tests in many years have demonstrated the efficacy and safety of clopidogrel for thrombotic cardio-cerebrovascular diseases (Lancet, 1996, 348: 1329). Clopidogrel is a precursor drug, which is metabolized in vivo through two oxidative steps by the liver P450 enzyme system to generate an active metabolite, which is covalently bound to $P2Y_{12}$ receptor on the platelet surface to inhibit platelet aggregation through $P2Y_{12}$ receptor antagonism (Thromb Haemost, 2000, 84: 891). However, the researches on in-vivo metabolism of clopidogrel reveal that 85% of the prototype drug is hydrolyzed by human carboxylesterase 1 (hCE1) in the liver into an inactive carboxylic derivative of clopidogrel (J Pharmacol Exp Ther, 2006, 319: 1467), which greatly reduces the oral bioavailability of clopidogrel, resulting in the disadvantages of clopidogrel such as high dosage in clinical use (load dosage: 300 mg clopidogrel), slow onset of action, and delayed inhibition of platelets (Cardiovascular Drug Reviews, 1993, 11: 180). In addition, due to the differential expression of the P450 enzyme system in the liver among different individuals, clopidogrel that functions by metabolism by the P450 enzyme system has significant individual differences in clinical efficacy, including, for example, the presence of "clopidogrel resistance", and occurrence of cardiovascular events including stent thrombosis (ST) (Circulation, 2004, 109: 166).

Prasugrel, a new anti-platelet agent, is developed by Sankyo Pharmaceuticals Co., Ltd. and Eli Lilly Company. Compared with clopidogrel, prasugrel can more quickly and effectively inhibit platelet aggregation, but has a higher risk of bleeding. In elective percutaneous coronary intervention (PCI) for treating acute coronary syndrome, compared with clopidogrel, prasugrel can significantly lower the incidence of ischemic events (including stent thrombosis), but the bleeding risk is increased (N Engl J Med, 2007, 357: 2001). Other adverse effects of prasugrel include, for example, thrombocytopenia and neutropenia.

Certain 2-hydroxytetrahydrothienopyridine derivatives having anti-platelet aggregation effect are disclosed in U.S. Pat. Nos. 5,190,938, 5,874,581, and WO9749397. These compounds are, however, racemic mixtures, and to date, there have been no studies proving whether their racemates and enantiomers are different in efficacy and safety. In Chinese Patent Application No. 200810097756.7, certain aromatic heterocyclic carboxylate ester derivatives of prasugrel and clopidogrel, especially certain racemic derivatives of prasugrel, are disclosed, but optically active alkyl carboxylate derivatives and other related derivatives of 2-hydroxytetrahydrothienopyridine are not involved.

Therefore, there is a need in clinic for development of a new anti-platelet aggregation agent that has a rapid onset of action and high efficacy, and can avoid the bleeding side effect.

SUMMARY OF THE INVENTION

Therefore, in order to overcome the above disadvantages, an objective of the present invention is to design and synthesize new ester derivatives of 2-hydroxytetrahydrothienopyridine, so as to develop anti-platelet aggregation agents that have good efficacy and low side effects.

The present invention discloses an optically active 2-hydroxytetrahydrothienopyridine derivative, for example, a compound of general Formula I, or a pharmaceutically acceptable salt or hydrate thereof:

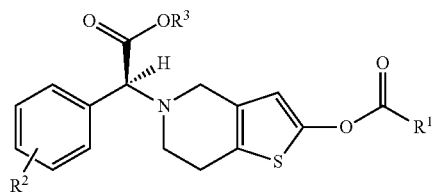

where $R^1$ is a non-substituted or X-substituted linear or branched $C_{1-10}$ alkyl, $OR^4$, $NR^5R^6$, phenyl, a Y-substituted phenyl, styryl, 4-hydroxystyryl, 4-hydroxy-3-methoxystyryl, 3-pyridinyl, alkenyl, or alkynyl, in which X is fluoro, chloro, bromo, iodo, cyano, nitro, amino, amido, sulfonamido, trifluoromethyl, mercapto, hydroxyl, acetoxy, methoxy, ethoxy, carboxyl, methoxycarbonyl, ethoxycarbonyl, aryloxy, phenyl or a Y-substituted phenyl; Y is fluoro, chloro, bromo, iodo, cyano, nitro, amino, amido, sulfonamido, trifluoromethyl, mercapto, hydroxy, acetoxy, methoxy, ethoxy, carboxyl, methoxycarbonyl or ethoxycarbonyl, and the Y group is at position 2, 3 or 4 of the phenyl ring;

$R^2$ is H, fluoro, chloro, bromo, iodo, cyano, nitro, amino, amido, sulfonamido, trifluoromethyl, mercapto, hydroxyl, acetoxy, methoxy, ethoxy, carboxyl, methoxycarbonyl, ethoxycarbonyl, a linear or branched $C_{1-6}$ alkyl, alkenyl or alkynyl, and is at position 2, 3 or 4 of the phenyl ring; and when $R^2$ is 2-chloro, $R^1$ is not phenyl, and when $R^2$ is 2-halo, $R^1$ is not 3-pyridinyl;

$R^3$ is a linear or branched $C_{1-6}$ alkyl or a $C_{1-6}$ cycloalkyl; $R^4$ is a linear or branched $C_{1-10}$ alkyl, or benzyl; and $R^5$ and $R^6$ each are a linear or branched $C_{1-6}$ alkyl, or $NR^5R^6$ is

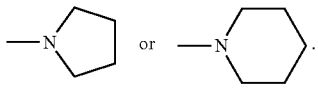

In the present compound of Formula I, $R^1$ is preferably a non-substituted or X-substituted linear or branched $C_{1-6}$ alkyl, $OR^4$, $NR^5R^6$, phenyl, a Y-substituted phenyl, styryl, 4-hydroxylstyryl, 4-hydroxy-3-methoxystyryl, or 3-pyridinyl, in which X is amino, amido, sulfonamido, hydroxyl, acetoxy, methoxy, ethoxy, carboxyl, methoxycarbonyl, ethoxycarbonyl, aryloxy, phenyl, or a Y-substituted phenyl; Y is fluoro, chloro, bromo, iodo, cyano, nitro, amino, amido, sulfonamido, hydroxyl, acetoxy, methoxy, ethoxy, carboxyl, methoxycarbonyl, or ethoxycarbonyl, and is at position 2, 3 or 4 of the phenyl ring; $R^4$ is a linear or branched $C_{1-6}$ alkyl, or benzyl; and $R^5$ and $R^6$ is a linear or branched $C_{1-6}$ alkyl, or $NR^5R^6$ is

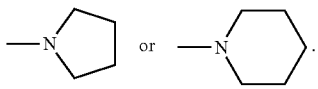

In the present compound of Formula I, $R^1$ is more preferably methyl, ethyl, propyl, t-butyl, tert-pentyl, phenoxymethyl, methoxy, ethoxy, isopropoxy, isobutoxy, benzyloxy, —N(CH₃)₂, —N(CH₂CH₃)₂, —N(CH₃)(CH₂CH₃),

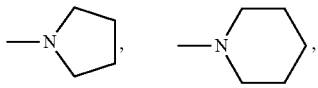

phenyl, 2-hydroxyphenyl, 2-acetoxyphenyl, 4-methoxyphenyl, 4-nitrophenyl, styryl, 4-hydroxylstyryl, 4-hydroxy-3-methoxystyryl, or 3-pyridinyl.

In the present compound of Formula I, $R^2$ is preferably 2-fluoro, 2-chloro, 2-bromo, 2-cyano, or 2-trifluoromethyl, and when $R^2$ is 2-chloro, $R^1$ is not phenyl, and when $R^2$ is 2-halo, $R^1$ is not 3-pyridinyl.

In the present compound of Formula I, $R^2$ is preferably 2-fluoro or 2-chloro.

In the present compound of Formula I, $R^3$ is more preferably methyl or ethyl.

Preferred compounds of the present invention are:
(S)-methyl 2-(2-acetoxy-6,7-dihydrothieno[3,2-c]pyridin-5(4H)-yl)-2-(2-chlorophenyl)-acetate I-2;
(S)-methyl 2-(2-propanoyloxy-6,7-dihydrothieno[3,2-c]pyridin-5(4H)-yl)-2-(2-chloro phenyl)-acetate I-3;
(S)-methyl 2-(2-butanoyloxy-6,7-dihydrothieno[3,2-c]pyridin-5(4H)-yl)-2-(2-chlorophenyl)-acetate I-4;
(S)-methyl 2-(2-(2-acetoxybenzoyloxy)-6,7-dihydrothieno[3,2-c]pyridin-5(4H)-yl)-2-(2-chlorophenyl)-acetate I-5;
(S)-methyl 2-(2-pivaloyloxy-6,7-dihydrothieno[3,2-c]pyridin-5(4H)-yl)-2-(2-chlorophenyl)-acetate I-7;
(S)-methyl 2-(2-(2,2-dimethylbutanoyloxy)-6,7-dihydrothieno[3,2-c]pyridin-5(4H)-yl)-2-(2-chlorophenyl)-acetate I-8;
(S)-methyl 2-(2-cinnamoyloxy-6,7-dihydrothieno[3,2-c]pyridin-5(4H)-yl)-2-(2-chlorophenyl)-acetate I-9;
(S)-methyl 2-(2-(4-methoxybenzoyloxy)-6,7-dihydrothieno[3,2-c]pyridin-5(4H)-yl)-2-(2-chlorophenyl)-acetate I-11;
(S)-methyl 2-(2-phenylacetoxy-6,7-dihydrothieno[3,2-c]pyridin-5(4H)-yl)-2-(2-chlorophenyl)-acetate I-12;
(S)-methyl 2-(2-(phenoxyacetoxy)-6,7-dihydrothieno[3,2-c]pyridin-5(4H)-yl)-2-(2-chlorophenyl)-acetate I-13;
(S)-methyl 2-(2-(ethoxycarbonyloxy)-6,7-dihydrothieno[3,2-c]pyridin-5(4H)-yl)-2-(2-chlorophenyl)-acetate I-14;
(S)-methyl 2-(2-(isobutoxycarbonyloxy)-6,7-dihydrothieno[3,2-c]pyridin-5(4H)-yl)-2-(2-chlorophenyl)-acetate I-15;
(S)-methyl 2-(2-(isopropoxycarbonyloxy)-6,7-dihydrothieno[3,2-c]pyridin-5(4H)-yl)-2-(2-chlorophenyl)-acetate I-16;
(S)-methyl 2-(2-(benzyloxycarbonyloxy)-6,7-dihydrothieno[3,2-c]pyridin-5(4H)-yl)-2-(2-chlorophenyl)-acetate I-17;
(S)-methyl 2-(2-(N,N-dimethylcarbamoyloxy)-6,7-dihydrothieno[3,2-c]pyridin-5(4H)-yl)-2-(2-chlorophenyl)-acetate I-18;
(S)-methyl 2-(2-acetoxy-6,7-dihydrothieno[3,2-c]pyridin-5(4H)-yl)-2-(2-fluorophenyl)-acetate I-19;
(S)-methyl 2-(2-acetoxy-6,7-dihydrothieno[3,2-c]pyridin-5(4H)-yl)-2-(4-chlorophenyl)-acetate I-20;
(S)-methyl 2-(2-acetoxy-6,7-dihydrothieno[3,2-c]pyridin-5(4H)-yl)-2-phenyl-acetate I-21;
(S)-methyl 2-(2-(pyrrolidine-1-carbonyloxy)-6,7-dihydrothieno[3,2-c]pyridin-5(4H)-yl)-2-(2-chlorophenyl)-acetate I-22;
(S)-methyl 2-(2-(methoxycarbonyloxy)-6,7-dihydrothieno[3,2-c]pyridin-5(4H)-yl)-2-(2-chlorophenyl)-acetate I-23;
(S)-methyl 2-(2-acetoxy-6,7-dihydrothieno[3,2-c]pyridin-5(4H)-yl)-2-(2-bromophenyl)-acetate I-24;
(S)-ethyl 2-(2-acetoxy-6,7-dihydrothieno[3,2-c]pyridin-5(4H)-yl)-2-(2-fluorophenyl)-acetate I-25;
(S)-ethyl 2-(2-acetoxy-6,7-dihydrothieno[3,2-c]pyridin-5(4H)-yl)-2-(2-chlorophenyl)-acetate I-26;
(S)-ethyl 2-(2-acetoxy-6,7-dihydrothieno[3,2-c]pyridin-5(4H)-yl)-2-(2-bromophenyl)-acetate I-27;
(S)-methyl 2-(2-propanoyloxy-6,7-dihydrothieno[3,2-c]pyridin-5(4H)-yl)-2-(2-fluoro phenyl)-acetate I-28;
(S)-methyl 2-(2-propanoyloxy-6,7-dihydrothieno[3,2-c]pyridin-5(4H)-yl)-2-(2-bromo phenyl)-acetate I-29;
(S)-ethyl 2-(2-propanoyloxy-6,7-dihydrothieno[3,2-c]pyridin-5(4H)-yl)-2-(2-fluoro phenyl)-acetate I-30;
(S)-ethyl 2-(2-propanoyloxy-6,7-dihydrothieno[3,2-c]pyridin-5(4H)-yl)-2-(2-chlorophenyl)-acetate I-31;
(S)-ethyl 2-(2-propanoyloxy-6,7-dihydrothieno[3,2-c]pyridin-5(4H)-yl)-2-(2-bromo phenyl)-acetate I-32;
(S)-methyl 2-(2-butanoyloxy-6,7-dihydrothieno[3,2-c]pyridin-5(4H)-yl)-2-(2-fluorophenyl)-acetate I-33;
(S)-methyl 2-(2-butanoyloxy-6,7-dihydrothieno[3,2-c]pyridin-5(4H)-yl)-2-(2-bromophenyl)-acetate I-34;
(S)-ethyl 2-(2-butanoyloxy-6,7-dihydrothieno[3,2-c]pyridin-5(4H)-yl)-2-(2-fluorophenyl)-acetate I-35;
(S)-ethyl 2-(2-butanoyloxy-6,7-dihydrothieno[3,2-c]pyridin-5(4H)-yl)-2-(2-chlorophenyl)-acetate I-36;
(S)-ethyl 2-(2-butanoyloxy-6,7-dihydrothieno[3,2-c]pyridin-5(4H)-yl)-2-(2-bromophenyl)-acetate I-37;
(S)-ethyl 2-(2-pivaloyloxy-6,7-dihydrothieno[3,2-c]pyridin-5(4H)-yl)-2-(2-chlorophenyl)-acetate I-38;
(S)-ethyl 2-(2-(2,2-dimethylbutanoyloxy)-6,7-dihydrothieno[3,2-c]pyridin-5(4H)-yl)-2-(2-chlorophenyl)-acetate I-39;
(S)-methyl 2-(2-feruloyloxy-6,7-dihydrothieno[3,2-c]pyridin-5(4H)-yl)-2-(2-chlorophenyl)-acetate I-40;
(S)-methyl 2-(2-benzoyloxy-6,7-dihydrothieno[3,2-c]pyridin-5(4H)-yl)-2-(2-fluorophenyl)-acetate I-41;

(S)-methyl 2-(2-nicotinoyloxy-6,7-dihydrothieno[3,2-c]pyridin-5(4H)-yl)-2-(4-chlorophenyl)-acetate I-42;
(S)-methyl 2-(2-(2-hydroxybenzoyloxy)-6,7-dihydrothieno[3,2-c]pyridin-5(4H)-yl)-2-(2-chlorophenyl)-acetate I-43;
(S)-methyl 2-(2-(t-butoxycarbonyloxy)-6,7-dihydrothieno[3,2-c]pyridin-5(4H)-yl)-2-(2-chlorophenyl)-acetate I-44;
(S)-methyl 2-(2-(N,N-diethylcarbamoyloxy)-6,7-dihydrothieno[3,2-c]pyridin-5(4H)-yl)-2-(2-chlorophenyl)-acetate I-45; and
(S)-methyl 2-(2-(piperidine-1-carbonyloxy)-6,7-dihydrothieno[3,2-c]pyridin-5(4H)-yl)-2-(2-chlorophenyl)-acetate I-46.

The present compound of Formula I has an optical purity of 70-100%, preferably 90-100%, more preferably 95-100%, and most preferably 98-100%.

The derivative of the present invention also includes an enantiomer and a racemate of the compound of Formula I.

The derivative of the present invention also includes a pharmaceutically acceptable salt of the compound of Formula I, including, but not limited to, an acid addition salt formed by the compound of the present invention with an acid below: hydrochloric acid, hydrobromic acid, sulfuric acid, citric acid, tartaric acid, phosphoric acid, lactic acid, acetic acid, maleic acid, fumaric acid, malic acid, mandelic acid, methanesulfonic acid, benzenesulfonic acid, p-toluenesulfonic acid, pamoic acid, oxalic acid, or succinic acid.

Another objective of the present invention is to provide a method for preparing an optically active 2-hydroxytetrahydrothienopyridine derivative represented by Formula I, as shown in reaction schemes below.

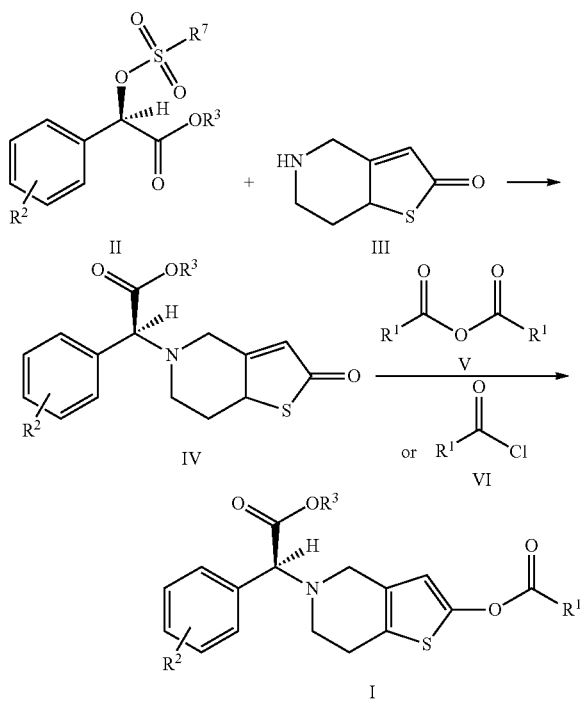

Method (1)

In the above reaction scheme, $R^1$, $R^2$, and $R^3$ are as defined above in the compound of Formula I; and $R^7$ is a $C_{1-6}$ alkyl, trifluoromethyl, pentafluoroethyl, heptafluoropropyl, phenyl, or a Z-substituted phenyl, in which Z is a $C_{1-3}$ alkyl, halo, cyano, nitro, or trifluoromethyl, and is at position 2, 3 or 4 of the phenyl ring.

The method specifically comprises the following steps:

(1) A compound of Formula II ((R)-2-($R^7$-sulfonyloxy)-2-($R^2$ substituted phenyl)acetate) is reacted with a compound of Formula III (5,6,7,7a-tetrahydrothieno[3,2-c]pyridin-2(4H)-one) or a salt thereof (at a molar ratio of 1:2-2:1) in the presence of a base (in an amount of 1-10 eq of the compound of Formula II), to obtain a compound of Formula IV ((2S)-2-(2-oxo-7,7a-dihydrothieno[3,2-c]pyridin-5(2H,4H,6H)-yl)-2-($R^2$ substituted phenyl)acetate) or a salt thereof, where the solvent used is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide, and preferably N,N-dimethyl formamide, tetrahydrofuran, acetonitrile, or dichloromethane; the base used may be triethylamine, diisopropyl ethylamine, 1,8-diazabicyclo[5,4,0]undec-7-ene, potassium carbonate, sodium carbonate, potassium bicarbonate, or sodium bicarbonate; the reaction temperature is from −20° C. to 100° C., and preferably from 10° C. to 60° C.; and the salt of the compound of Formula III is selected from hydrochloride, p-toluenesulfonate, acetate, sulfate, phosphate, trifluoromethanesulfonate, oxalate, methanesulfonate, benzenesulfonate, or hydrobromide; and (2) The compound of Formula IV or the salt thereof is reacted with a compound of Formula V (an anhydride) or a compound of Formula VI ($R^1$-carbonyl chloride) (at a molar ratio of 1:1-1:10) in the presence of a base (in an amount of 1-10 eq of the compound of Formula IV), to obtain the compound of Formula I ((S)-2-(2-$R^1$-carbonyloxy-6,7-dihydrothieno[3,2-c]pyridin-5(4H)-yl)-2-($R^2$ substituted phenyl)-acetate); where the reaction solvent used is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide, and preferably tetrahydrofuran, acetonitrile, or N,N-dimethyl formamide; the base used is selected from triethylamine, sodium hydride, potassium hydride, 1,8-diazabicyclo[5,4,0]undec-7-ene, pyridine, diisopropylethylamine, lithium diisopropylamide, potassium carbonate, sodium carbonate, potassium bicarbonate, sodium bicarbonate, potassium t-butoxide, or sodium t-butoxide; and the reaction temperature is from −20° C. to 100° C., and preferably from 0° C. to 50° C.

Method (2)

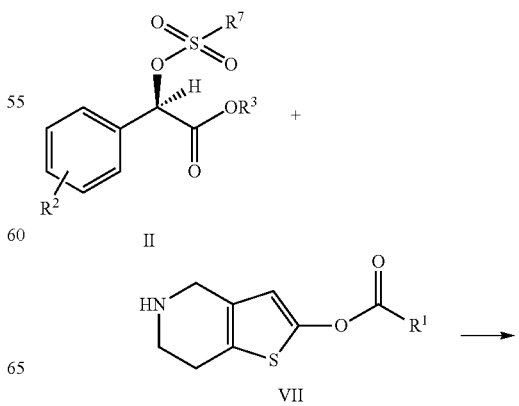

-continued

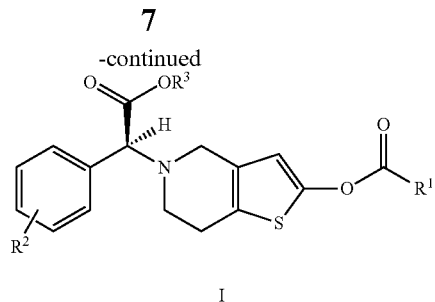

I

In the reaction scheme, $R^1$, $R^2$, $R^3$, and $R^7$ are as defined above in the compounds of Formulae I and II.

The method specifically comprises the following step:

the compound of Formula II is reacted with a compound of Formula VII (4,5,6,7-tetrahydrothieno[3,2-c]pyridin-2-yl carboxylate) or a salt thereof in the presence of a base, to obtain the compound of Formula I; where the solvent used is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide, and preferably N,N-dimethyl formamide, tetrahydrofuran, acetonitrile, or dichloromethane; the base used is selected from triethylamine, diisopropyl ethylamine, 1,8-diazabicyclo[5,4,0]undec-7-ene, potassium carbonate, sodium carbonate, potassium bicarbonate, or sodium bicarbonate; the reaction temperature is from −20° C. to 100° C., and preferably 10° C. to 60° C.; and the salt of the compound of Formula VII is selected from hydrochloride, p-toluenesulfonate, acetate, sulfate, phosphate, trifluoromethanesulfonate, oxalate, methanesulfonate, benzenesulfonate, or hydrobromide.

The compound of Formula VII or the salt thereof may be prepared following the method described in U.S. Pat. No. 5,190,938.

The enantiomer of the present compound of general Formula I may be prepared following Methods (I) and (2) above, except that an enantiomer of the compound of Formula II is used as a starting material.

The racemate of the present compound of general Formula I may be prepared following Methods (I) and (2) above, except that a racemate of the compound of Formula II is used as a starting material.

A further objective of the present invention is to provide a use of an optically active 2-hydroxytetrahydrothienopyridine derivative represented by Formula I in the preparation of a medicament.

Pharmacodynamic experiment results show that the present compounds of general Formula I have significant inhibition effect of platelet aggregation, and the anti-platelet aggregation effect of some compounds is obviously superior to that of clopidogrel. In addition, the compound of Formula I (S configuration) generally exhibits a more potent platelet aggregation inhibition than the corresponding enantiomer (R configuration) and racemic mixture thereof. Pharmacokinetic experiment results show that the present compound of Formula I can be effectively converted in vivo into a pharmacologically active metabolite, so as to exert the platelet aggregation inhibition, and the bioavailability of an intermediate metabolite from which the active metabolite is formed is obviously higher than that of clopidogrel. The above experiment results suggest that the compound of the present invention or a pharmaceutically acceptable salt thereof is useful in the preparation of a medicament for preventing or treating thrombosis and embolism related diseases, especially atherosclerosis, myocardial infarction, stroke, ischemic cerebral thrombosis, peripheral arterial disease, acute coronary syndrome, or thrombosis after percutaneous coronary intervention (PCI).

The present invention also provides a pharmaceutical composition for preventing or treating thrombosis and embolism related diseases, comprising a therapeutically effective amount of the compound of Formula I or a pharmaceutically acceptable salt thereof as an active ingredient, and a pharmaceutically acceptable carrier. The pharmaceutical composition may be in any of conventional pharmaceutical dosage forms such as ordinary tablets or capsules, sustained release tablets or capsules, controlled release tablets or capsules, granules, powders, syrups, oral solutions, and injections.

The dosage of the compound of Formula I in the pharmaceutical composition of the present invention varies depending on factors such as the symptoms and age. For an adult, it is orally administered per dose at a lower limit of 0.1 mg (preferably 1 mg) and an upper limit of 1000 mg (preferably 500 mg), or is intravenously administrated per dose at a lower limit of 0.01 mg (preferably 0.1 mg) and an upper limit of 500 mg (preferably 250 mg). The dosage may fall outside the above ranges according to the severity of the disease and the dosage form.

DETAILED DESCRIPTION OF THE PREFERRED EMBODIMENTS

Figure 1:
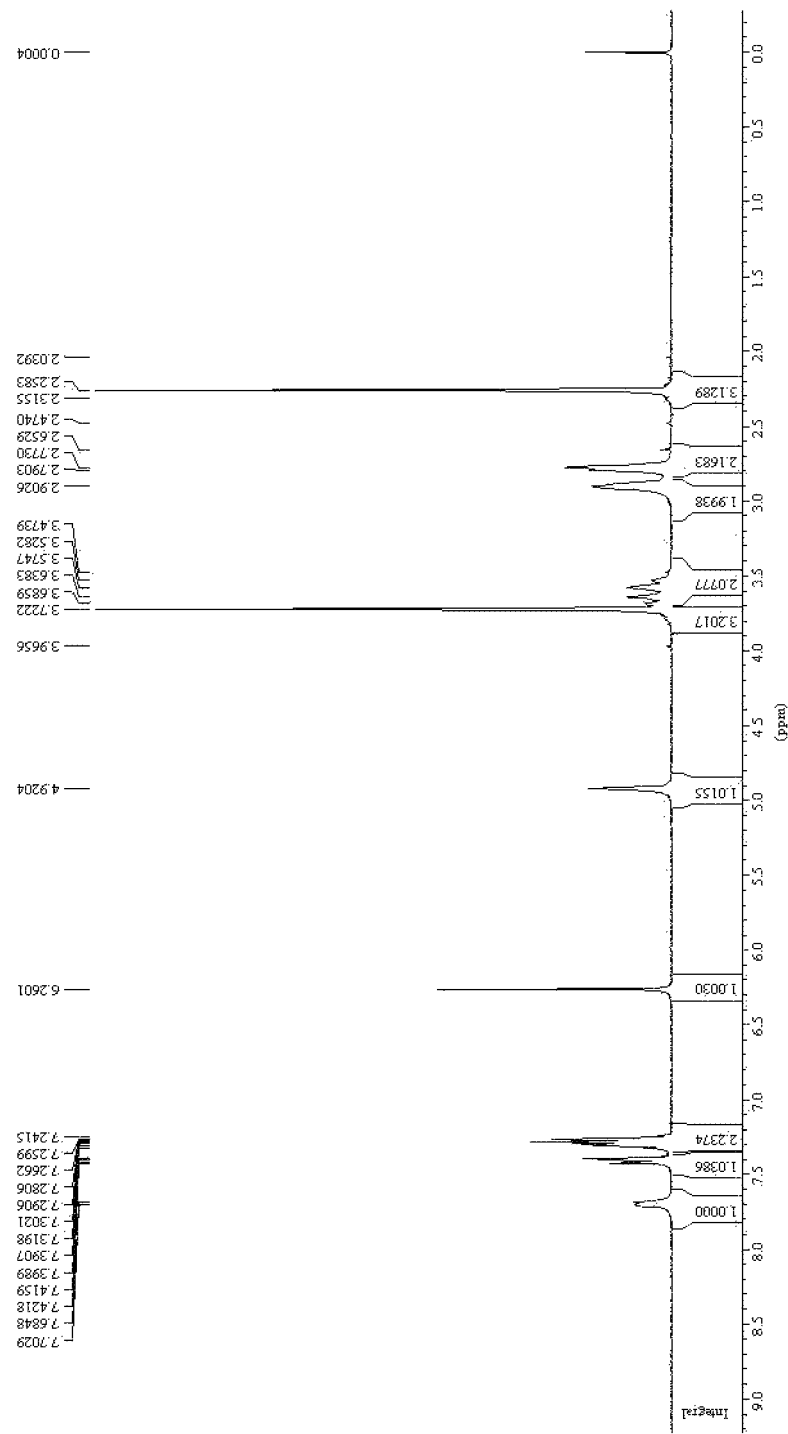
FIG. 1 shows $^1$H NMR spectra of Compound I-2.
Figure 2:
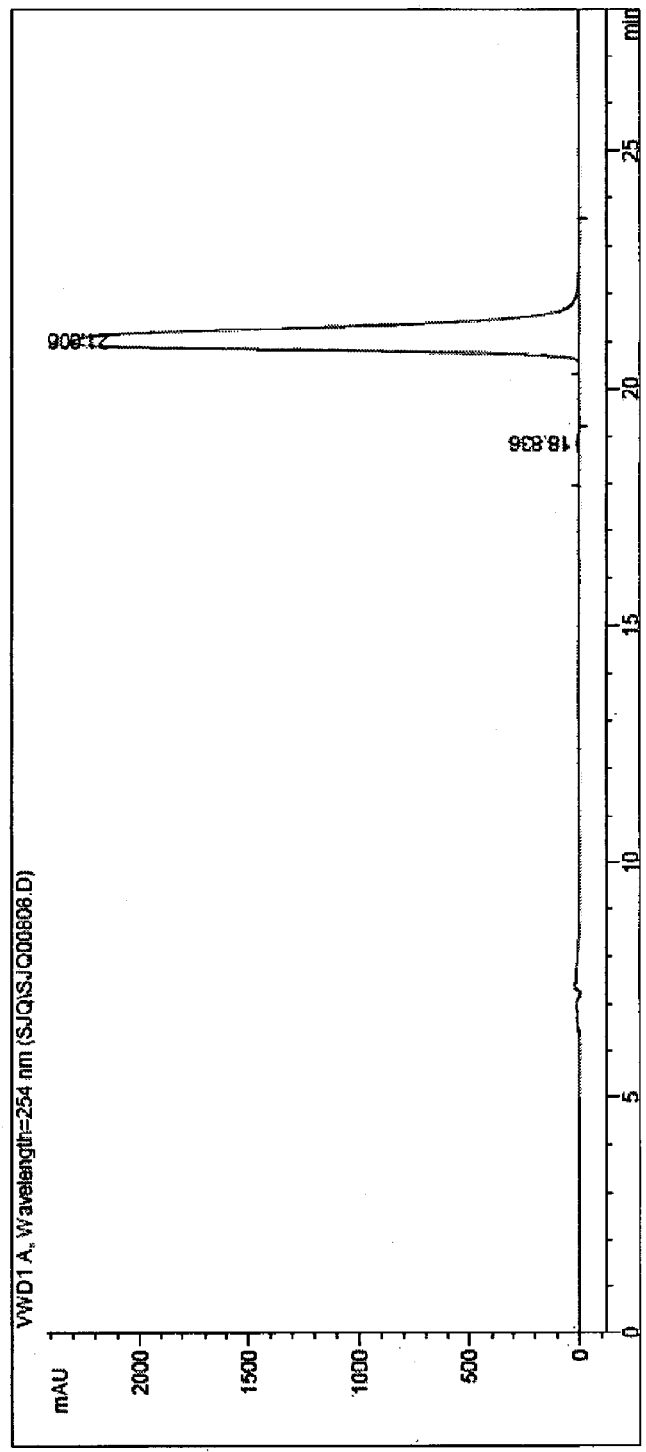
FIG. 2 shows chiral HPLC analysis of Compound I-2.
Figure 3:
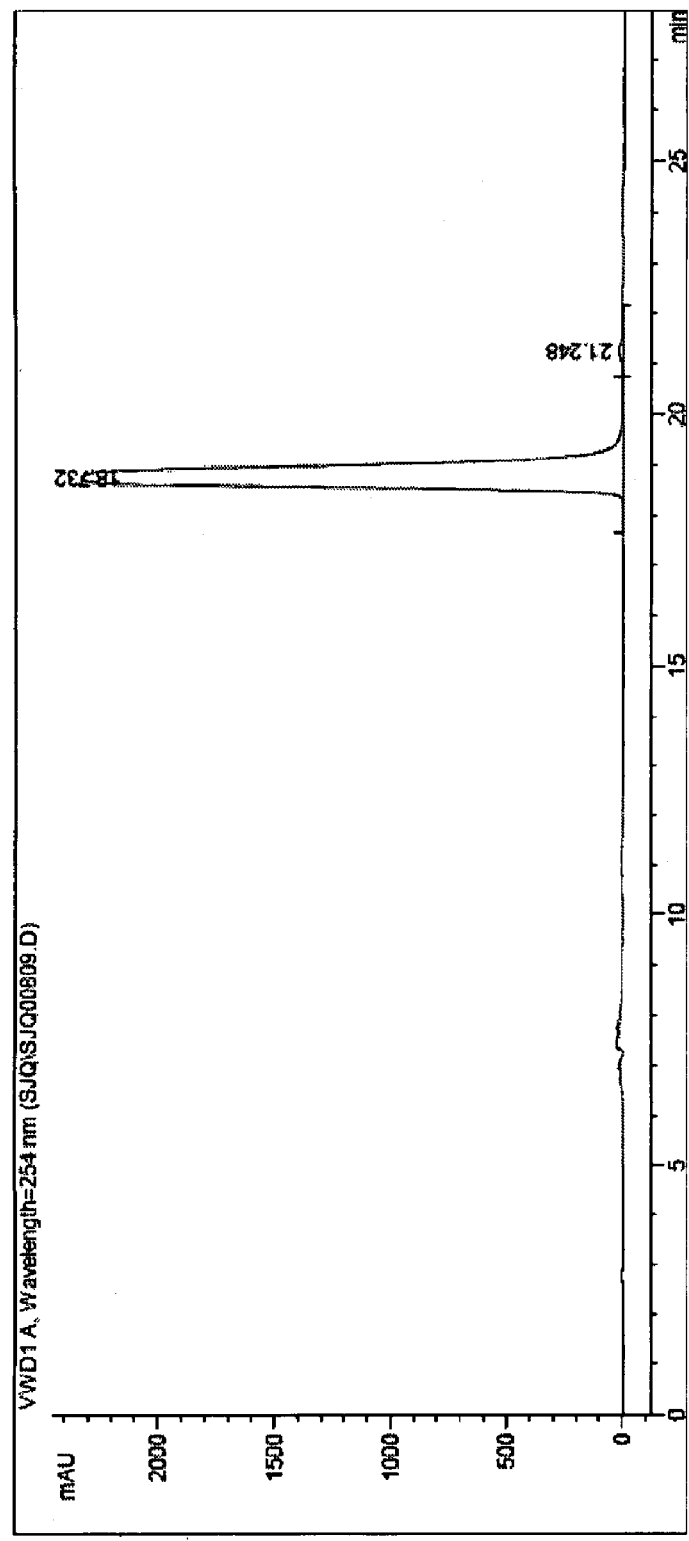
FIG. 3 shows chiral HPLC analysis of Compound I-2' (an enantiomer of I-2).
Figure 4:
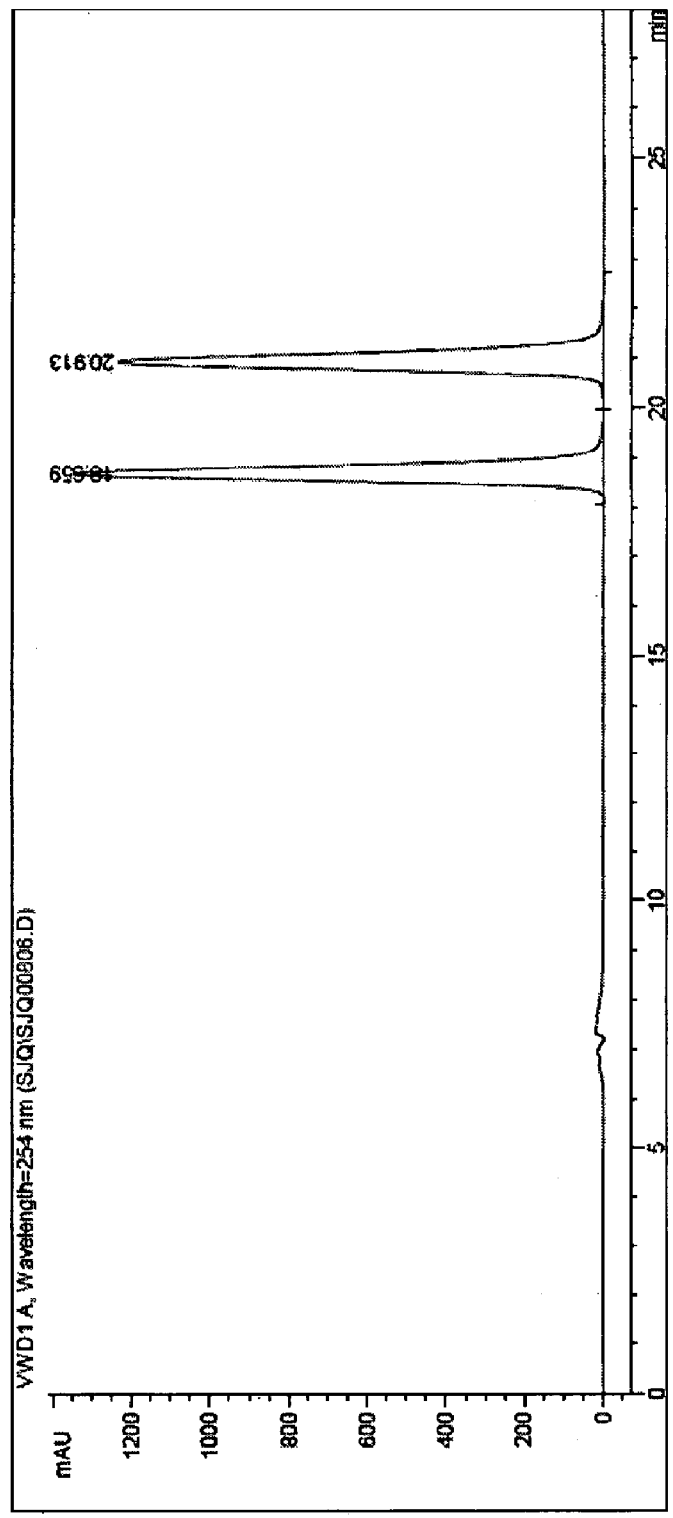
FIG. 4 shows chiral HPLC analysis of Compound I-2" (a racemic mixture of I-2).

The contents of the present invention will be described in detail by means of examples. The examples are provided herein for illustrative purposes only, and are not intended to limit the scope of the present invention.

Example 1

(R)-Methyl o-chloromandelate

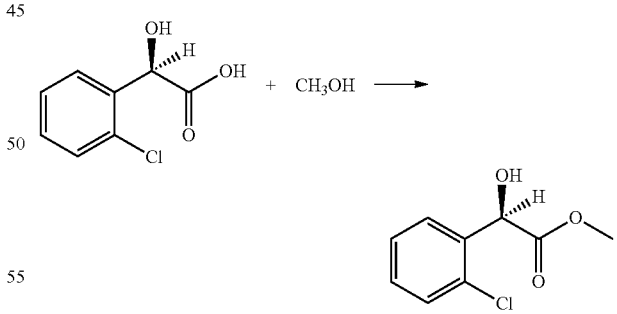

(R)-o-chloromandelic acid (5.6 g) was dissolved in 23.1 ml of methanol, and then a catalytic amount of concentrated sulfuric acid (0.12 ml) was added, and heated to reflux for 2 hrs. After cooling, methanol was evaporated under reduced pressure, and the residue was dissolved in dichloromethane, and washed sequentially with 10% aqueous potassium carbonate solution and water. The dichloromethane solution was dried, and evaporated to dryness, to give 5.79 g of (R)-methyl o-chloromandelate as a clear colorless oil. Yield 96%. $^1$H-NMR (300 MHz, CDCl$_3$) δ 3.52 (d, 1H, J=4.8 Hz), 3.78 (s, 3H), 5.57 (d, 1H, J=4.5 Hz), 7.26-7.31 (m, 2H), 7.37-7.41 (m, 2H); ESI-MS m/z 222.9 [M+Na]⁺.

Example 2

(R)-Methyl 2-(2-chlorophenyl)-2-(4-nitrophenylsulfonyloxy)-acetate (II-1)

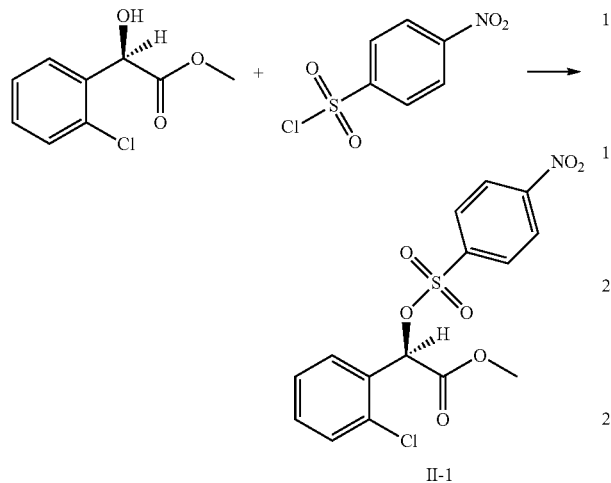

(R)-Methyl o-chloromandelate (98.4 g, 0.49 mol, ee=99%) was dissolved in 500 ml of anhydrous dichloromethane, and then 91 ml of triethylamine (0.65 mol) and a catalytic amount of DMAP were added. 120 g (0.54 mol) of p-nitrophenylsulfonyl chloride was dissolved in 500 ml of anhydrous dichloromethane, which was added dropwise into the reaction solution at 0° C., and reacted for 4-5 hrs at 0° C. Water (500 ml) was added to the reaction solution and the layers were separated. The aqueous phase was extracted with dichloromethane (150 ml×3), and the organic phases were combined and dried, and dichloromethane was evaporated under reduced pressure to afford 206.5 g of a crude product as a dark red oil, which was recrystallized in methanol to obtain 154.5 g of a solid product (II-1). Yield 82%. ¹H-NMR (300 MHz, CDCl₃) δ 3.57 (s, 3H), 6.39 (s, 1H), 7.21-7.39 (m, 4H), 8.07 (d, 2H, J=8.9 Hz), 8.30 (d, 2H, J=8.9 Hz); ESI-MS ink 408.0 [M+Na]⁺.

Example 3

(2S)-Methyl 2-(2-oxo-7,7a-dihydrothieno[3,2-c]pyridin-5(2H,4H,6H)-yl)-2-(2-chlorophenyl)-acetate (IV-1)

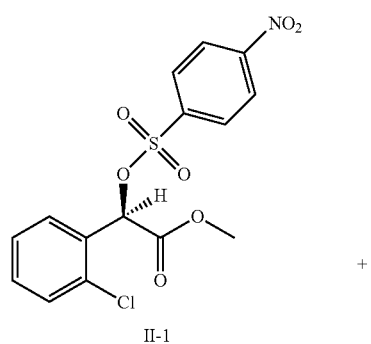

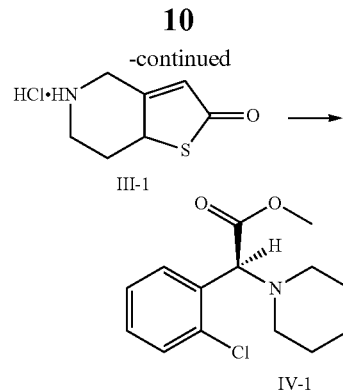

58.1 g (0.15 mol) of (R)-methyl 2-(2-chlorophenyl)-2-(4-nitrophenylsulfonyloxy)-acetate (II-1), 32.3 g (0.17 mol) of 5,6,7,7a-tetrahydrothieno[3,2-c]pyridin-2(4H)-one hydrochloride (III-1), and 37.8 g (0.38 mol) of potassium bicarbonate were added to 500 ml of acetonitrile. The reaction was stirred under a nitrogen atmosphere at room temperature for 26 hrs. The reaction solution was allowed to stand and the insoluble material was filtered off, to obtain a dark red mother liquor. The solvent was evaporated under reduced pressure, and 35.4 g of an oil product was obtained after purification by flash column chromatography (petroleum ether:ethyl acetate=4:1). Yield 70%. Recrystallization from ethanol afforded 18.1 g of a pure product (IV-1) as a white solid. mp: 146-148° C., ee=97.5%, [α]$_D^{19}$=+114.0° (c 0.5, MeOH); ¹H-NMR (300 MHz, CDCl₃) δ 1.79-1.93 (m, 1H), 2.30-2.40 (m, 1H), 2.56-2.70 (m, 1H), 3.00-3.27 (m, 2H), 3.72 (s, 3H), 3.79-3.93 (m, 1H), 4.12-4.19 (m, 1H), 4.89 (d, 1H, J=5.6 Hz), 6.00 (d, 1H, J=5.2 Hz), 7.26-7.50 (m, 4H); ¹³C-NMR (75 MHz, CDCl₃) δ 33.9, 34.0, 49.0, 49.7, 51.1, 51.6, 52.2, 52.4, 67.3, 76.6, 77.0, 77.4, 126.6, 126.8, 127.2, 129.8, 130.1, 132.7, 134.8, 167.2, 167.4, 170.8, 198.6; ESI-MS m/z 338.1 [M+H]⁺; HRMS Calcd for C₁₆H₁₇NO₃SCl [M+H]⁺ m/z 338.0618, found 338.0626.

Example 4

(S)-Methyl 2-(2-benzoyloxy-6,7-dihydrothieno[3,2-c]pyridin-5(4H)-yl)-2-(2-chlorophenyl)-acetate (I-1)

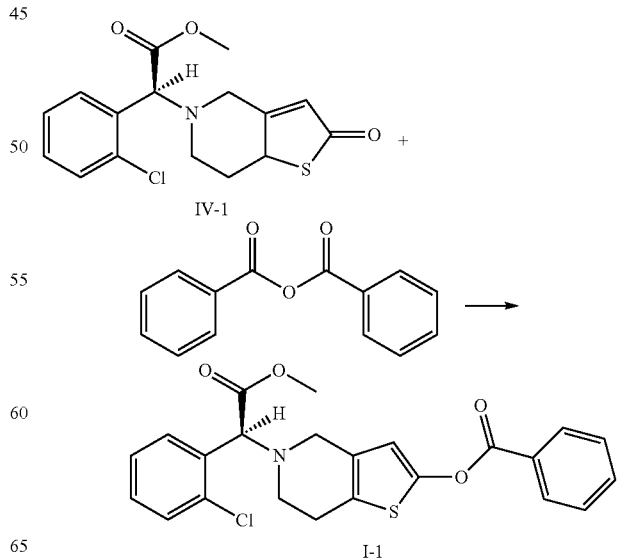

(2S)-Methyl 2-(2-chlorophenyl)-2-(2-oxo-5,6,7,7a-tetrahydrothieno[3,2-c]pyridinyl)acetate (IV-1) (113 mg) was dissolved in acetonitrile (10 ml), 0.10 ml of triethylamine was added, and 151 mg of benzoic anhydride was added dropwise at 0° C., and then the mixture was warmed to room temperature and reacted for 2 hrs. The reaction solution was poured into water (30 ml), the aqueous phase was extracted with ethyl acetate (50 ml×3), and the organic phase was washed with saturated aqueous sodium bicarbonate solution and saturated saline, dried over anhydrous sodium sulfate, and evaporated, to obtain a crude product, which was subjected to flash column chromatography (petroleum ether: ethyl acetate=40:3), to obtain (S)-methyl 2-(2-benzoyloxy-6,7-dihydrothieno[3,2-c]pyridin-5(4H)-yl)-2-(2-chlorophenyl)-acetate (I-1) (77 mg). Yield 52%, mp: 84-86° C., ee=93.5% (chiral HPLC analysis conditions: Chiralpak IC 4.6 mm×250 mm; column temperature: 25° C.; mobile phase: 90% n-hexane/10% isopropanol/0.1% diethylamine; flow rate: 0.5 ml/min; and detection wavelength: UV 254 nm), $[\alpha]_D^{20}$=+34.00° (c 0.50, MeOH); $^1$H-NMR (300 MHz, CDCl$_3$) δ 2.82-2.93 (m, 4H), 3.57-3.68 (m, 2H), 3.73 (s, 3H), 4.95 (s, 1H), 6.42 (s, 1H), 7.26-8.17 (m, 9H); $^{13}$C-NMR (75 MHz CDCl$_3$) δ 25.0, 48.2, 50.4, 52.2, 67.8, 112.1, 125.9, 127.2, 128.5, 128.6, 129.5, 129.8, 130.0, 130.2, 133.9, 134.7, 149.9, 163.5; ESI-MS m/z 442.1 [M+H]$^+$; HRMS Calcd for C$_{23}$H$_{21}$NO$_4$SCl [M+H]$^+$ m/z 442.0891, found 442.0880.

Example 5

(S)-Methyl 2-(2-acetoxy-6,7-dihydrothieno[3,2-c]pyridin-5(4H)-yl)-2-(2-chlorophenyl)-acetate (I-2)

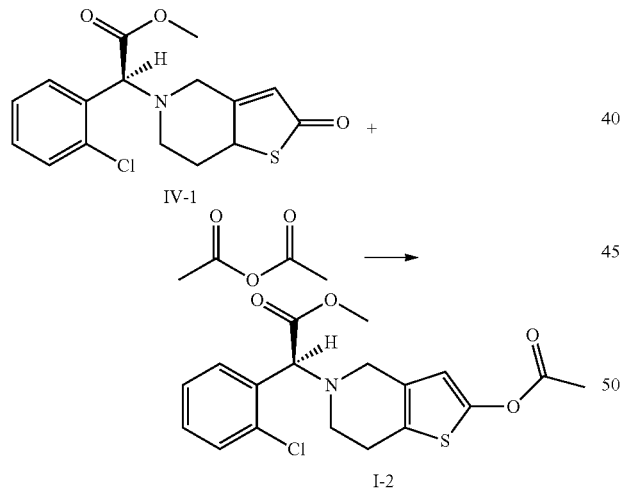

Following the method described in Example 4, (2S)-methyl 2-(2-chlorophenyl)-2-(2-oxo-5, 6, 7, 7a-tetrahydrothieno[3,2-c]pyridinyl)acetate (IV-1) (6.5 g) was reacted with acetic anhydride (3.6 ml), to prepare (S)-methyl 2-(2-acetoxy-6,7-dihydrothieno[3,2-c]pyridin-5(4H)-yl)-2-(2-chlorophenyl)-acetate (I-2) (6.8 g). Yield 93%. Recrystallization from ethanol afforded a white solid, mp: 73-75° C., ee=98.9% (chiral HPLC analysis conditions: Chiralpak IC 4.6 mm×250 mm; column temperature: 25° C.; mobile phase: 92% n-hexane/8% tetrahydrofuran/0.1% diethylamine; flow rate: 0.5 ml/min; and detection wavelength: UV 254 nm), $[\alpha]_D^{23}$=+45.00° (c=1.0, CH$_3$OH); $^1$H-NMR (300 MHz, CDCl$_3$) δ 2.26 (s, 3H), 2.65-2.90 (m, 4H), 3.47-3.69 (m, 2H), 3.72 (s, 3H), 4.92 (s, 1H), 6.26 (s, 1H), 7.24-7.70 (m, 4H); $^{13}$C-NMR (75 MHz, CDCl$_3$) δ 20.2, 24.5, 47.6, 49.8, 51.6, 67.3, 111.5, 125.3, 126.6, 128.8, 128.9, 129.3, 129.4, 133.3, 134.2, 149.1, 167.2, 170.7; ESI-MS m/z 380.0 [M+H]$^+$; HRMS Calcd for C$_{18}$H$_{19}$NO$_4$SCl [M+H]$^+$ m/z 380.0723, found 380.0737.

Example 6

(R)-Methyl 2-(2-acetoxy-6,7-dihydrothieno[3,2-c]pyridin-5(4H)-yl)-2-(2-chlorophenyl)-acetate (I-2')

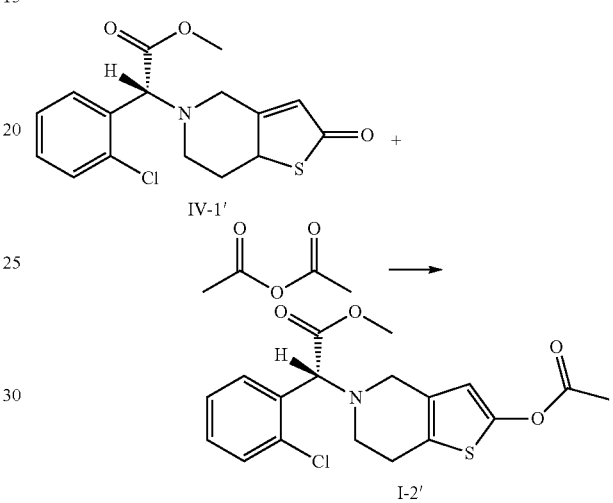

Following the method described in Example 4, (2R)-methyl 2-(2-chlorophenyl)-2-(2-oxo-7,7a-dihydrothieno[3,2-c]pyridin-5(2H,4H,6H)-yl)-acetate (IV-1') (prepared following Examples I-3) was reacted with acetic anhydride, to prepare (R)-methyl 2-(2-acetoxy-6,7-dihydrothieno[3,2-c]pyridin-5(4H)-yl)-2-(2-chlorophenyl)-acetate (I-2'), ee=98.2% (chiral HPLC analysis conditions were the same as those in Example 5), $[\alpha]_D^{23}$=−44.00° (c=1.0, CH$_3$OH).

Example 7

(S)-Methyl 2-(2-propanoyloxy-6,7-dihydrothieno[3,2-c]pyridin-5(4H)-yl)-2-(2-chlorophenyl)-acetate (I-3)

Following the method described in Example 4, (2S)-methyl 2-(2-chlorophenyl)-2-(2-oxo-7,7a-dihydrothieno[3,2-c]pyridin-5(2H,4H,6H)-yl)-acetate (IV-1) (338 mg) was reacted with propionic anhydride (0.27 ml), to prepare (S)-methyl 2-(2-propanoyloxy-6,7-dihydrothieno[3,2-c]pyridin-5(4H)-yl)-2-(2-chlorophenyl)-acetate (I-3) (267 mg). Yield 66%, ee=96.5% (chiral HPLC analysis conditions were the same as those in Example 4), $[\alpha]_D^{20}$=+36.00° (c 0.50, MeOH); $^1$H-NMR (300 MHz, CDCl$_3$) δ 1.23 (t, 3H, J=7.4 Hz), 2.55 (q, 2H, J=7.7 Hz), 2.76-2.78 (m, 2H), 2.87-2.88 (m, 2H), 3.53 (d, 1H, J=14.2 Hz), 3.65 (d, 1H, J=13.6 Hz), 3.72 (s, 3H), 4.91 (s, 1H), 6.26 (s, 1H), 7.26-7.69 (m, 4H); $^{13}$C-NMR (75 MHz, CDCl$_3$) δ 8.8, 21.1, 25.0, 27.4, 48.2, 50.3, 52.2, 67.8, 106.2, 111.7, 125.6, 127.2, 129.1, 129.5, 129.8, 130.0, 123.7, 149.8, 171.2; ESI-MS m/z 394.1 [M+H]$^+$; HRMS Calcd for C$_{19}$H$_{21}$NO$_4$SCl [M+H]$^+$ m/z 394.0883, found 394.0880.

Example 8

(S)-methyl 2-(2-butanoyloxy-6,7-dihydrothieno[3,2-c]pyridin-5(4H)-yl)-2-(2-chlorophenyl)-acetate (I-4)

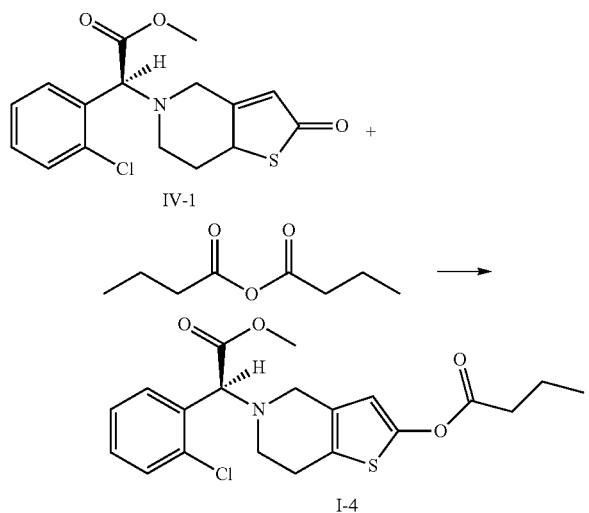

Following the method described in Example 4, (2S)-methyl 2-(2-chlorophenyl)-2-(2-oxo-7,7a-dihydrothieno[3,2-c]pyridin-5(2H,4H,6H)-yl)-acetate (IV-1) (86 mg) was reacted with butyric anhydride (90 μl), to prepare (S)-methyl 2-(2-butanoyloxy-6,7-dihydrothieno[3,2-c]pyridin-5(4H-yl)-2-(2-chlorophenyl)-acetate (I-4) (51 mg). Yield 49%, ee 96.3% (chiral HPLC analysis conditions were the same as those in Example 4), $[\alpha]_D^{20}$=+32.00° (c 0.50, MeOH); $^1$H-NMR (300 MHz, CDCl$_3$) δ 1.00 (t, 3H, J=5.2 Hz), 1.74 (q, 2H, J=5.2 Hz), 2.47-2.52 (m, 2H), 2.76-2.78 (m, 2H), 2.86-2.89 (m, 2H), 3.53 (d, 1H, J=14.3 Hz), 3.65 (d, 1H, J=14.2 Hz), 3.72 (s, 3H), 4.90 (s, 1H), 6.25 (s, 1H), 7.24-7.69 (m, 4H); $^{13}$C-NMR (75 MHz, CDCl$_3$) δ 13.5, 18.2, 25.0, 35.8, 48.2, 50.3, 52.1, 67.9, 111.8, 125.7, 127.1, 129.2, 129.4, 129.8, 130.0, 133.8, 134.7, 149.7, 170.4, 171.2; ESI-MS m/z 408.1 [M+H]$^+$; HRMS Calcd for C$_{20}$H$_{23}$NO$_4$SCl [M+H]$^+$ m/z 408.1035, found 408.1036.

Example 9

(S)-methyl 2-(2-(2-acetoxybenzoyloxy)-6,7-dihydrothieno[3,2-c]pyridin-5(4H)-yl)-2-(2-chlorophenyl)-acetate (I-5)

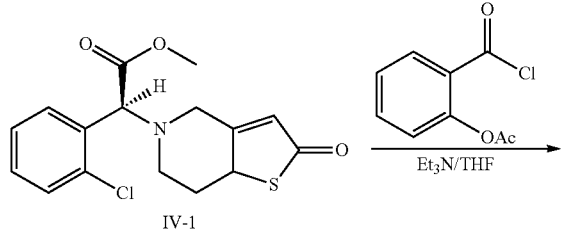

338 mg of (2S)-methyl 2-(2-chlorophenyl)-2-(2-oxo-7,7a-dihydrothieno[3,2-c]pyridin-5(2H,4H,6H)-yl)-acetate (IV-1) was dissolved in 15 ml of tetrahydrofuran, 0.83 ml of triethylamine was added dropwise and stirred for 10 minutes, and then 600 mg of acetylsalicylic chloride was added and stirred at room temperature for 24 hrs. The reaction solution was poured into saturated aqueous NaHCO$_3$ solution (20 ml), extracted with ethyl acetate (50 ml×3), concentrated, evaporated, and subjected to flash column chromatography (petroleum ether:ethyl acetate=5:1), to obtain (S)-methyl 2-(2-(2-acetoxybenzoyloxy)-6,7-dihydrothieno[3,2-c]pyridin-5(4H)-yl)-2-(2-chlorophenyl)-acetate (I-5) (280 mg). Yield: 56%, ee=96.1% (chiral HPLC analysis conditions: Chiralpak IC 4.6 mm×250 mm; column temperature: 25° C.; mobile phase: 85% n-hexane/15% tetrahydrofuran/0.1% diethylamine; flow rate: 0.5 ml/min; and detection wavelength: UV 254 nm), $[\alpha]_D^{20}$=+14.00° (c 0.50, CHCl$_3$); $^1$H-NMR (300 MHz, CDCl$_3$) δ 2.34 (s, 3H), 2.79-2.81 (m, 2H), 2.90-2.93 (m, 2H), 3.54-3.66 (m, 2H), 3.72 (s, 3H), 4.93 (s, 1H), 6.37 (s, 1H), 7.14-7.36 (m, 4H), 7.39-8.15 (m, 4H); $^{13}$C-NMR (75 MHz, CDCl$_3$) δ 20.93, 24.93, 48.04, 50.12, 52.12, 67.65, 112.61, 117.34, 118.97, 121.66, 124.09, 126.14, 127.12, 129.35, 129.45, 129.79, 129.92, 130.71, 132.12, 133.54, 134.71, 135.73, 149.32, 151.12, 161.32, 169.47, 171.17; ESI-MS m/z 500 [M+H]$^+$, 522 [M+Na]$^+$; HRMS Calcd for C$_{25}$H$_{23}$NO$_6$SCl [M+H]$^+$ m/z 500.0931, found 500.0935.

Example 10

(S)-methyl 2-(2-nicotinoyloxy-6,7-dihydrothieno[3,2-c]pyridin-5(4H)-yl)-2-(2-chlorophenyl)-acetate (I-6)

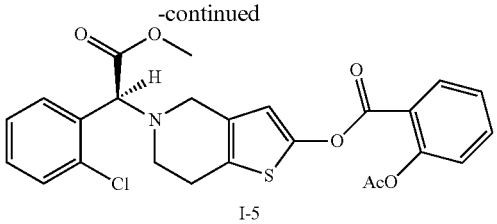

Following the method described in Example 9, (2S)-methyl 2-(2-chlorophenyl)-2-(2-oxo-7,7a-dihydrothieno[3,2-c]pyridin-5(2H,4H,6H)-yl)-acetate (IV-1) (338 mg) was reacted with nicotinoyl chloride (512 mg), to prepare (S)-methyl 2-(2-nicotinoyloxy-6,7-dihydrothieno[3,2-c]pyridin-5(4H)-yl)-2-(2-chlorophenyl)-acetate (I-6) (173 mg). Yield: 39%, mp: 92-94° C., ee=97.7% (chiral HPLC analysis conditions: Chiralpak IC 4.6 mm×250 mm; column temperature: 25° C.; mobile phase: 50% n-hexane/50% isopropanol/0.1% diethylamine; flow rate: 0.8 ml/min; and detection wavelength: UV 254 nm), $[\alpha]_D^{20}$=+34.00° (c 0.50, MeOH); $^1$H-NMR (500 MHz, CDCl$_3$) δ 2.80-2.82 (m, 2H), 2.91-2.93 (m, 2H), 3.58 (d, 1H, J=14.3 Hz), 3.69 (d, 1H, J=14.3 Hz), 3.71 (s, 3H), 4.93 (s, 1H), 6.45 (s, 1H), 7.25-7.45 (m, 4H), 7.69 (m, 1H), 8.38-8.41 (m, 1H), 8.83-8.84 (m, 1H), 9.34 (m, 1H); $^{13}$C-NMR (75 MHz, CDCl$_3$) δ 24.93, 48.05, 50.24, 52.11, 67.73, 112.43, 123.47, 124.66, 126.33, 127.11, 129.32, 129.43, 129.78, 129.89, 133.59, 134.68, 137.54, 149.18, 151.19, 154.07, 162.17, 171.16; ESI-MS m/z 443.1 [M+H]$^+$, 465.1 [M+Na]$^+$; HRMS Calcd for C$_{22}$H$_{20}$N$_2$O$_4$SCl [M+H]$^+$ m/z 443.0839, found 443.0832.

Example 11

(S)-methyl 2-(2-pivaloyloxy-6,7-dihydrothieno[3,2-c]pyridin-5(4H)-yl)-2-(2-chlorophenyl)-acetate (I-7)

Preparation Method (1)

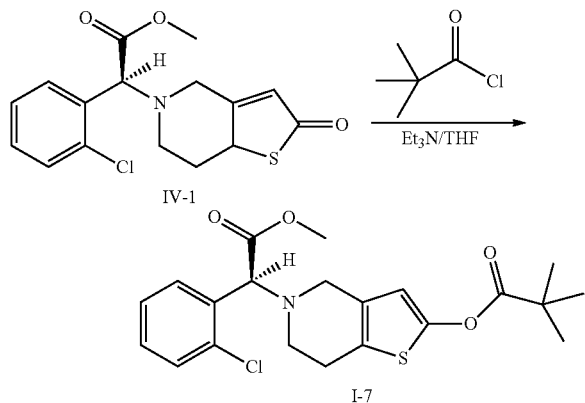

Following the method described in Example 9, (2S)-methyl 2-(2-chlorophenyl)-2-(2-oxo-7,7a-dihydrothieno[3.2-c pyridin-5(2H,4H,6H)-yl)-acetate (IV-1) (338 mg) was reacted with pivaloyl chloride (738 μl), to prepare (S)-methyl 2-(2-pivaloyloxy-6,7-dihydrothieno[3,2-c]pyridin-5(4H)-yl)-2-(2-chlorophenyl)-acetate (I-7) (360 mg). Yield: 85%, mp: 105-107° C., ee=99.1% (chiral HPLC analysis conditions were the same as those in Example 5), $[\alpha]_D^{20}$=+38.00. (c 0.50, MeOH); $^1$H-NMR (300 MHz, CDCl$_3$) δ 1.30 (s, 9H), 2.77-2.79 (m, 2H), 2.87-2.88 (m, 2H), 3.53 (d, 1H, J=14.2 Hz), 3.65 (d, 1H, J=14.2 Hz), 3.72 (s, 3H), 4.90 (s, 1H), 6.26 (s, 1H), 7.23-7.69 (m, 4H); $^{13}$C-NMR (75 MHz, CDCl$_3$) δ 24.93, 26.95, 39.09, 48.12, 50.29, 52.09, 67.77, 111.43, 125.53, 127.10, 129.01, 129.38, 129.76, 129.92, 133.73, 134.68, 150.08, 171.20, 175.17; ESI-MS m/z 422.2 [M+H]$^+$; HRMS Calcd for C$_{21}$H$_{25}$NO$_4$SCl [M+H]$^+$ m/z 422.1198, found 422.1193.

Preparation Method (2)

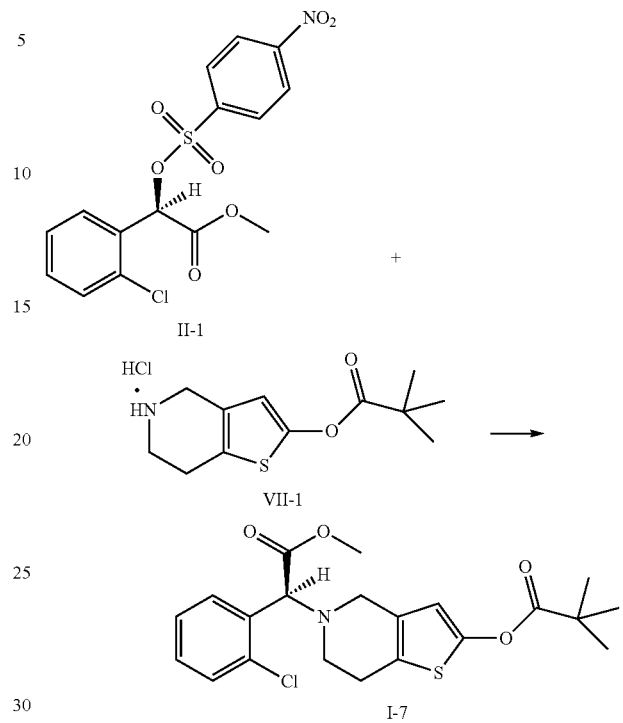

58.1 mg (0.15 mmol) of (R)-methyl 2-(2-chlorophenyl)-2-(4-nitrophenylsulfonyloxy)-acetate (II-1), 47 mg (0.17 mmol) of 4,5,6,7-tetrahydrothieno[3.2-c]pyridin-2-yl pivalate hydrochloride (VII-1) (prepared following the method described in U.S. Pat. No. 5,190,938) and 38 mg (0.38 mmol) of potassium bicarbonate were added to 5 ml of acetonitrile. The reaction was stirred under a nitrogen atmosphere at room temperature overnight. After the reaction solution was allowed to stand, the insoluble material was filtered off, and the solvent was evaporated under reduced pressure. After flash column chromatography (petroleum ether:ethyl acetate=4:1), (S)-methyl 2-(2-pivaloyloxy-6,7-dihydrothieno[3,2-c]pyridin-5(4H)-yl)-2-(2-chlorophenyl)-acetate (I-7) (43 mg) was obtained. Yield 69%.

Example 12

(S)-Methyl 2-(2-(2,2-dimethylbutanoyloxy)-6,7-dihydrothieno[3,2-c]pyridin-5(4H)-yl)-2-(2-chlorophenyl)-acetate (I-8)

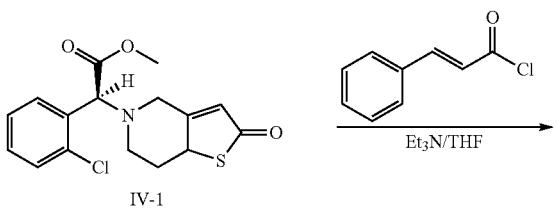

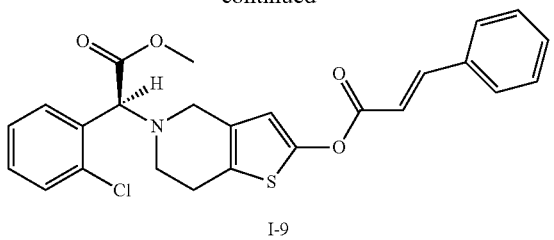

I-9

Following the method described in Example 9, (2S)-methyl 2-(2-chlorophenyl)-2-(2-oxo-7, 7a-dihydrothieno[3.2-c]pyridin-5(2H,4H,6H)-yl)-acetate (IV-1) (338 mg) was reacted with 2,2-dimethylbutanoyl chloride (824 μl), to prepare (S)-methyl 2-(2-(2,2-dimethylbutanoyloxy)-6,7-dihydrothieno[3,2-c]pyridin-5(4H)-yl)-2-(2-chlorophenyl)-acetate (I-8) (326 mg). Yield: 75%, mp: 98-100° C., ee=99.5% (chiral HPLC analysis conditions were the same as those in Example 5), $[\alpha]_D^{20}$=+36.00° (c 0.50, MeOH); $^1$H-NMR (300 MHz, CDCl$_3$) δ 0.88 (t, 3H, J=7.4 Hz), 1.26 (s, 6H), 1.64 (q, 2H, J=7.3 Hz), 2.76-2.78 (m, 2H), 2.87-2.88 (m, 2H), 3.53 (d, 1H, J=14.3 Hz), 3.65 (d, 1H, J=14.3 Hz), 3.71 (s, 3H), 4.90 (s, 1H), 6.25 (s, 1H), 7.22-7.69 (m, 4H); $^{13}$C-NMR (75 MHz, CDCl$_3$) δ 9.2, 24.47, 24.99, 33.32, 43.11, 48.16, 50.31, 52.11, 67.82, 111.49, 125.59, 127.11, 129.10, 129.40, 129.78, 129.95, 133.78, 134.70, 150.03, 171.24, 174.73; ESI-MS m/z 436.2 [M+H]$^+$; HRMS Calcd for C$_{22}$H$_{27}$NO$_4$SCl [M+H]$^+$, m/z 436.1352, found 436.1349.

Example 13

(S)-methyl 2-(2-cinnamoyloxy-6,7-dihydrothieno[3,2-c]pyridin-5(4H)-yl)-2-(2-chlorophenyl)-acetate (I-9)

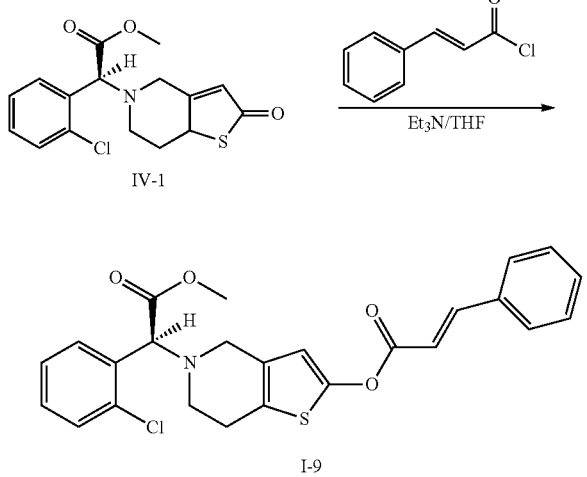

I-9

Following the method described in Example 9, (2S)-methyl 2-(2-chlorophenyl)-2-(2-oxo-7, 7a-dihydrothieno[3.2-c]pyridin-5(2H,4H,6H)-yl)-acetate (IV-1) (338 mg) was reacted with cinnamoyl chloride (1.0 g), to prepare (S)-methyl 2-(2-cinnamoyloxy-6,7-dihydrothieno[3,2-c]pyridin-5(4H)-yl)-2-(2-chloro phenyl)-acetate (I-9) (162 mg). Yield: 35%, mp: 122-124° C., ee=98.7% (chiral HPLC analysis conditions: Chiralpak IC 4.6 mm×250 mm; column temperature: 25° C.; mobile phase: 90% n-hexane/10% tetrahydrofuran/0.1% diethylamine; flow rate: 0.5 ml/min; and detection wavelength: UV 254 nm), $[\alpha]_D^{20}$=+14.00° (c 0.50, CHCl$_3$); $^1$H-NMR (300 MHz, CDCl$_3$) δ 2.79-2.81 (m, 2H), 2.89-2.90 (m, 2H), 3.51 (d, 1H, J=18.3 Hz), 3.63 (d, 1H, J=20.3 Hz), 3.72 (s, 3H), 4.92 (s, 1H), 6.35 (s, 1H), 6.56 (d, 1H, J=15.9 Hz), 7.24-7.32 (m, 2H), 7.39-7.42 (m, 4H), 7.55-7.58 (m, 2H), 7.69-7.71 (m, 1H), 7.85 (d, 1H, J=15.9 Hz); $^{13}$C-NMR (75 MHz, CDCl$_3$) δ 25.01, 48.17, 50.36, 52.15, 67.83, 111.78, 116.04, 125.84, 127.15, 128.36, 128.66, 128.99, 129.44, 129.81, 130.90, 133.98, 134.72, 147.39, 163.69, 171.20; ESI-MS m/z 468.2 [M+H]$^+$, 490.2 [M+Na]$^+$; HRMS Calcd for C$_{25}$H$_{23}$NO$_4$SCl [M+H]$^+$ m/z 468.1032, found 468.1036.

Example 14

(S)-methyl 2-(2-(4-nitrobenzoyloxy)-6,7-dihydrothieno[3,2-c]pyridin-5(4H)-yl)-2-(2-chlorophenyl)-acetate (I-10)

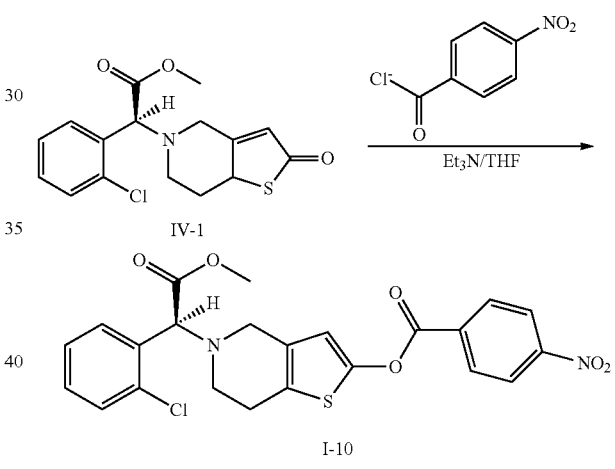

I-10

Following the method described in Example 9, (2S)-methyl 2-(2-chlorophenyl)-2-(2-oxo-7, 7a-dihydrothieno[3.2-c]pyridine-5(2H,4H,6H)-yl)-acetate (IV-1) (338 mg) was reacted with p-nitrobenzoyl chloride (1.13 g), to prepare (S)-methyl 2-(2-(4-nitrobenzoyloxy)-6,7-dihydrothieno[3,2-c]pyridin-5(4H)-yl)-2-(2-chlorophenyl)-acetate (I-10) (125 mg). Yield: 26%, mp: 100-102° C., ee=100% (chiral HPLC analysis conditions: Chiralpak IC 4.6 mm×250 mm; column temperature: 25° C.; mobile phase: 50% n-hexane/50% isopropanol/0.1% diethylamine; flow rate: 0.5 ml/min; and detection wavelength: UV 254 nm), $[\alpha]_D^{20}$=+30.00° (c 0.50, MeOH); $^1$H-NMR (300 MHz, CDCl$_3$) δ 2.82-2.84 (m, 2H), 2.91-2.95 (m, 2H), 3.59 (d, 1H, J=14.3 Hz), 3.69 (d, 1H, J=14.3 Hz), 3.73 (s, 3H), 4.95 (s, 1H), 6.47 (s, 1H), 7.26-7.70 (m, 4H), 8.18 (s, 4H); $^{13}$C-NMR (75 MHz, CDCl$_3$) δ 25.14, 29.76, 48.17, 49.76, 50.38, 51.15, 51.69, 52.28, 67.37, 67.86, 112.66, 123.86, 126.68, 127.26, 129.53, 129.85, 130.00, 131.39, 133.69, 133.98, 134.84, 149.27, 151.08, 161.75, 171.35; ESI-MS m/z 487.0 [M+H]$^+$; HRMS Calcd for C$_{23}$H$_{20}$N$_2$O$_6$SCl [M+H]$^+$ m/z 487.0736, found 487.0731.

Example 15

(S)-Methyl 2-(2-(4-methoxybenzoyloxy)-6,7-dihydrothieno[3,2-c]pyridin-5(4H)-yl)-2-(2-chlorophenyl)-acetate (I-11)

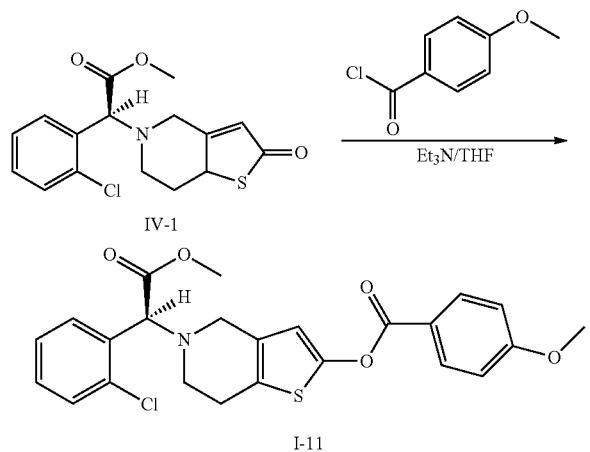

Following the method described in Example 9, (2S)-methyl 2-(2-chlorophenyl)-2-(2-oxo-7,7a-dihydrothieno[3,2-c]pyridin-5(2H,4H,6H)-yl)acetate (IV-1) (338 mg) was reacted with p-methoxybenzoyl chloride (1.02 g), to prepare (S)-methyl 2-(2-(4-methoxybenzoyloxy)-6,7-dihydrothieno[3,2-c]pyridin-5(4H)-yl)-2-(2-chlorophenyl)-acetate (I-11) (142 mg). Yield: 30%, ee=96.9% (chiral HPLC analysis conditions were the same as those in Example 14), $[\alpha]_D^{20}$=+26.00° (c 0.50, MeOH); $^1$H-NMR (300 MHz, CDCl$_3$) δ 2.79-2.90 (m, 4 H), 3.59-3.66 (m, 2H), 3.71 (s, 3H), 3.85 (s, 3H), 4.92 (s, 1H), 6.38 (s, 1H), 6.92-6.95 (m, 2H), 7.26-7.68 (m, 4H), 8.06-8.09 (m, 2H); $^{13}$C-NMR (75 MHz, CDCl$_3$) δ 25.05, 48.15, 50.36, 52.09, 55.49, 67.85, 111.86, 113.62, 114.14, 120.66, 121.24, 125.79, 127.13, 129.43, 129.79, 129.95, 132.31, 132.77, 133.78, 134.69, 149.95, 163.17, 164.58, 171.22; ESI-MS m/z 472.2 [M+H]$^+$, 494.2 [M+Na]$^+$; HRMS Calcd for C$_{24}$H$_{23}$NO$_5$SCl [M+H]$^+$ m/z 472.0993, found 472.0985.

Example 16

(S)-Methyl 2-(2-phenylacetoxy-6,7-dihydrothieno[3,2-c]pyridin-5(4H)-yl)-2-(2-chlorophenyl)-acetate (I-12)

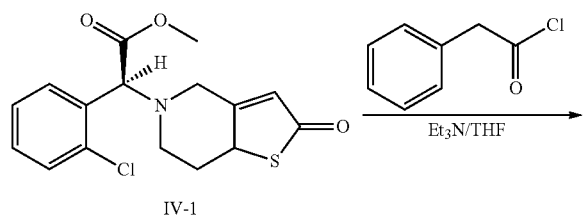

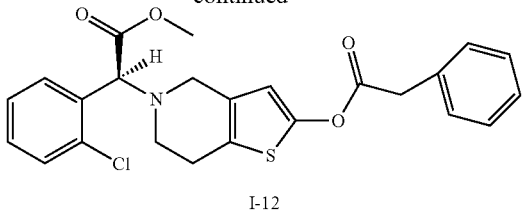

Following the method described in Example 9, (2S)-methyl 2-(2-chlorophenyl)-2-(2-oxo-7,7a-dihydrothieno[3,2-c]pyridin-5(2H,4H,6H)-yl)-acetate (IV-1) (338 mg) was reacted with phenylacetyl chloride (796 µl), to prepare (S)-methyl 2-(2-phenylacetoxy-6,7-dihydrothieno[3,2-c]pyridin-5(4H)-yl)-2-(2-chlorophenyl)-acetate (I-12) (210 mg). Yield: 46%, ee=93.5% (chiral HPLC analysis conditions were the same as those in Example 4), $[\alpha]^{20}$=+14.00° (c 0.50, MeOH); $^1$H-NMR (300 MHz, CDCl$_3$) δ 2.75-2.77 (m, 2H), 2.86-2.88 (m, 2H), 3.52 (d, 1H, J=14.3 Hz), 3.63 (d, 1H, J=14.3 Hz), 3.71 (s, 3H), 3.82 (s, 2H), 4.89 (s, 1H), 6.26 (s, 1H), 7.23-7.41 (m, 8H), 7.64-7.68 (m, 1H); $^{13}$C-NMR (75 MHz, CDCl$_3$) δ 24.98, 29.69, 40.87, 48.13, 50.29, 52.13, 67.80, 111.90, 125.81, 127.13, 127.45, 128.72, 129.14, 129.26, 129.43, 129.80, 129.92, 132.75, 133.70, 134.71, 149.62, 168.30, 171.25; ESI-MS m/z 456.2 [M+H]$^+$, 478.2 [M+Na]$^+$; HRMS Calcd for C$_{24}$H$_{23}$NO$_4$SCl [M+H]$^+$ m/z 456.1041, found 456.1036.

Example 17

(S)-Methyl 2-(2-(phenoxyacetoxy)-6,7-dihydrothieno[3,2-c]pyridin-5(4H)-yl)-2-(2-chlorophenyl)-acetate (I-13)

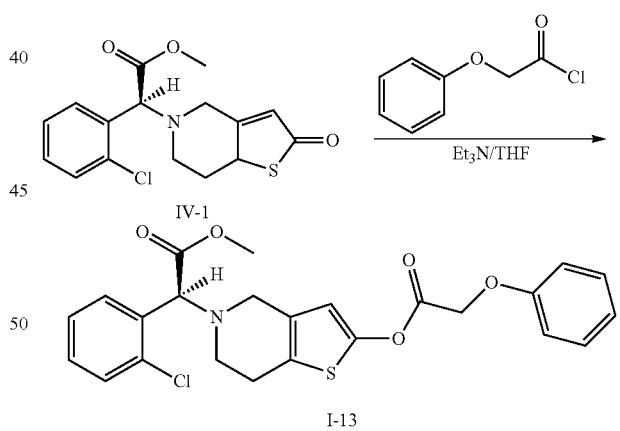

Following the method described in Example 9, (2S)-methyl 2-(2-chlorophenyl)-2-(2-oxo-7,7α-dihydrothieno[3,2-c]pyridin-5(2H,4H,6H)-yl)-acetate (IV-1) (169 mg) was reacted with phenoxyacetyl chloride (456 mg), to prepare (S)-methyl 2-(2-(phenoxyacetoxy)-6,7-dihydrothieno[3,2-c]pyridin-5(4H)-yl)-2-(2-chlorophenyl)-acetate (I-13) (85 mg). Yield: 36%, mp: 104-106° C., ee=89% (chiral HPLC analysis conditions were the same as those in Example 4), $[\alpha]_D^{20}$=+32.00° (c 0.50, MeOH); $^1$H-NMR (300 MHz, CDCl$_3$) δ 2.77-2.78 (m, 2H), 2.86-2.90 (m, 2H), 3.53 (d, 1H, J=14.3 Hz), 3.65 (d, 1H, J=14.3 Hz), 3.71 (s, 3H), 4.82 (s, 2H), 4.90 (s, 1H), 6.32 (s, 1H), 6.92-6.95 (m, 2H), 6.99-7.04

(m, 1H), 7.24-7.42 (m, 5H), 7.65-7.68 (m, 1H); $^{13}$C-NMR (75 MHz, CDCl$_3$) δ 24.95, 48.07, 50.23, 52.15, 65.14, 67.72, 112.41, 114.80, 122.13, 126.14, 127.15, 129.29, 129.48, 129.65, 129.83, 129.93, 133.58, 134.73, 148.79, 157.56, 165.88, 171.17; ESI-MS m/z 472.2 [M+H]$^+$, 494.2 [M+Na]$^+$; HRMS Calcd for C$_{24}$H$_{23}$NO$_5$SCl [M+H]$^+$ m/z 472.0993, found 472.0985.

Example 18

(S)-Methyl 2-(2-(ethoxycarbonyloxy)-6,7-dihydrothieno[3,2-c]pyridin-5(4H)-yl)-2-(2-chlorophenyl)-acetate (I-14)

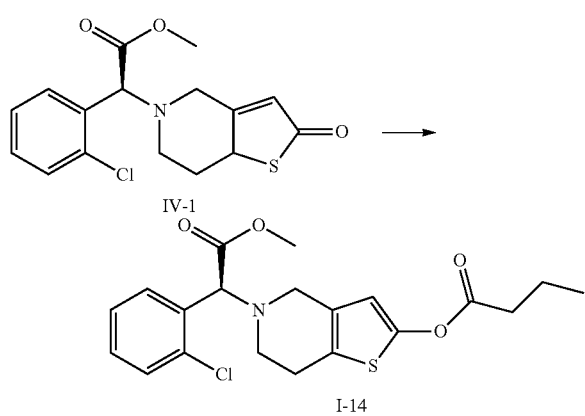

(2S)-Methyl 2-(2-chlorophenyl)-2-(2-oxo-7,7a-dihydrothieno[3.2-c]pyridin-5(2H,4H,6H)-yl)-acetate (IV-1) (85 mg) was dissolved in 10 ml of anhydrous tetrahydrofuran, and 0.141 ml of triethylamine was added at room temperature and stirred for 10 min. Then, 0.167 ml of ethyl chloroformate was added dropwise at 0° C. After the addition, the reaction solution became a light yellow cloudy solution from a dark red clear solution. The ice bath was removed and the reaction was warmed to 10° C. for 1 hr. Then, 0.07 ml of triethylamine and 0.1 ml of ethyl chloroformate were additionally added in an ice bath at 0° C. The ice bath was removed and the reaction was warmed to 10° C. for 1 hr, at which the raw materials substantially disappeared. Water (20 ml) was added, the reaction solution was extracted with ethyl acetate (30 ml×3) and dried over anhydrous sodium sulfate, and the solvent was evaporated to give a crude product, which was subjected to flash column chromatography (petroleum ether:ethyl acetate=40:3) to obtain (S)-methyl 2-(2-(ethoxycarbonyloxy)-6,7-dihydrothieno[3,2-c]pyridin-5(4H)-yl)-2-(2-chlorophenyl)-acetate (I-14) (77 mg). Yield 75%, mp: 42-44° C., ee=97.3% (chiral HPLC analysis conditions were the same as those in Example 4), $[α]_D^{20}$=+40.00° (c 0.50, MeOH); $^1$H-NMR (300 MHz, CDCl$_3$) δ 1.37 (t, 3H, J=7.2 Hz), 2.76-2.78 (m, 2H), 2.86-2.90 (m, 2H), 3.52 (d, 1H, J=14.2 Hz), 3.64 (d, 1H, J=14.3 Hz), 3.72 (s, 3H), 4.32 (q, 2H, J=7.1, 14.3 Hz), 4.90 (s, 1H), 6.30 (s, 1H), 7.24-7.68 (m, 4H); $^{13}$C-NMR (75 MHz, CDCl$_3$) δ 14.4, 25.4, 48.4, 50.5, 52.4, 65.7, 68.1, 112.7, 126.2, 127.4, 129.7, 129.8, 130.1, 130.2, 134.0, 135.0, 152.9, 157.3, 171.5; ESI-MS m/z 410.1 [M+H]$^+$, 432.1 [M+Na]$^+$; HRMS Calcd for C$_{19}$H$_{21}$NO$_5$SCl [M+H]$^+$ m/z 410.0836, found 410.0829.

Example 19

(S)-Methyl 2-(2-(isobutoxycarbonyloxy)-6,7-dihydrothieno[3,2-c]pyridin-5(4H)-yl)-2-(2-chlorophenyl)-acetate (I-15)

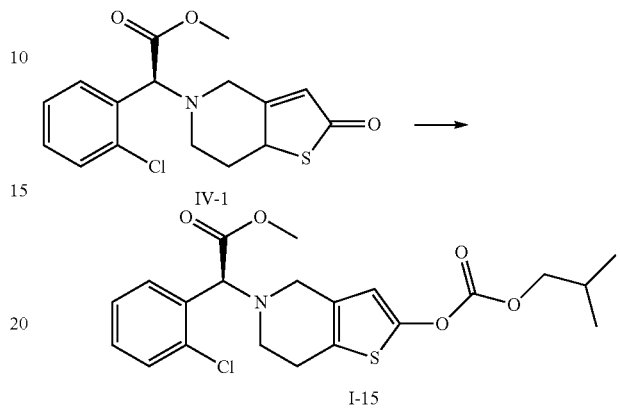

Following the method described in Example 18, (2S)-methyl 2-(2-chlorophenyl)-2-(2-oxo-7,7α-dihydrothieno[3,2-c]pyridin-5(2H,4H,6H)-yl)-acetate (IV-1) (85 mg) was reacted with isobutyl chloroformate (0.229 ml), to prepare (S)-methyl 2-(2-(isobutoxycarbonyloxy)-6,7-dihydrothieno[3,2-c]pyridin-5(4H)-yl)-2-(2-chlorophenyl)-acetate (I-15) (75 mg). Yield 69%, ee=95.5% (chiral HPLC analysis conditions were the same as those in Example 4), $[α]_D^{20}$=+16.00° (c 0.50, MeOH); $^1$H-NMR (300 MHz, CDCl$_3$) δ 0.98 (d, 6H, J=6.7 Hz), 2.01-2.05 (m, 1H), 2.76-2.78 (m, 2H), 2.86-2.90 (m, 2H), 3.52 (d, 1H, J=14.3 Hz), 3.64 (d, 1H, J=14.4 Hz), 3.72 (s, 3H), 4.25 (d, 2H, J=6.6 Hz), 4.90 (s, 1H), 6.29 (s, 1H), 7.26-7.42 (m, 4H); $^{13}$C-NMR (75 MHz, CDCl$_3$) δ 19.1, 25.4, 28.0, 48.4, 50.5, 52.4, 68.1, 75.6, 112.6, 126.1, 127.4, 129.7, 129.8, 130.1, 130.2, 134.0, 135.0, 150.8, 153.0, 171.5; ESI-MS m/z 460.3 [M+Na]$^+$; HRMS Calcd for C$_{21}$H$_{25}$NO$_5$SCl [M+H]$^+$ m/z 438.1150, found 438.1142.

Example 20

(S)-Methyl 2-(2-(isopropoxycarbonyloxy)-6,7-dihydrothieno[3,2-c]pyridin-5(4H)-yl)-2-(2-chlorophenyl)-acetate (I-16)

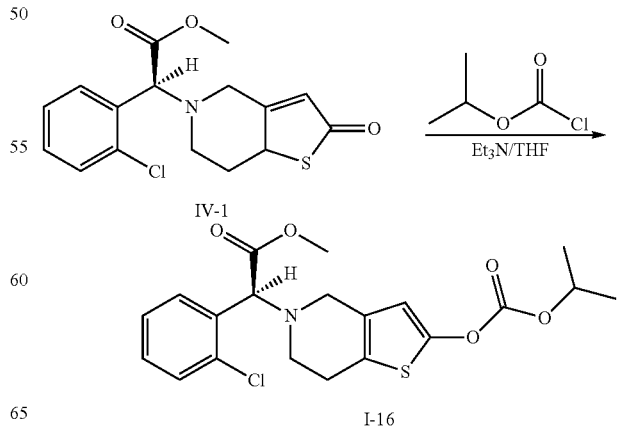

Following the method described in Example 18, (2S)-methyl 2-(2-chlorophenyl)-2-(2-oxo-7,7a-dihydrothieno[3.2-c]pyridin-5(2H,4H,6H)-yl)-acetate (IV-1) (85 mg) was reacted with isopropyl chloroformate (0.23 ml), to prepare (S)-methyl 2-(2-(isobutoxycarbonyloxy)-6,7-dihydrothieno[3,2-c]pyridin-5(4H)-yl)-2-(2-chlorophenyl)-acetate (I-15) (100 mg). Yield: 94%, ee=97.5% (chiral HPLC analysis conditions were the same as those in Example 4), $[\alpha]_D^{20}$=+34.00° (c 0.50, MeOH); $^1$H-NMR (300 MHz, CDCl$_3$) δ 1.36 (d, 6H, J=6.2 Hz), 2.77-2.78 (m, 2H), 2.86-2.89 (m, 2H), 3.52 (d, 1H, J=14.2 Hz), 3.64 (d, 1H, J=14.3 Hz), 3.72 (s, 3H), 4.90 (s, 1H), 4.93-5.01 (m, 1H), 6.30 (s, 1H), 7.24-7.68 (m, 4H); $^{13}$C-NMR (75 MHz, CDCl$_3$) δ 21.6, 25.4, 48.1, 50.3, 52.1, 67.8, 73.9, 112.2, 125.7, 127.1, 129.4, 129.8, 129.9, 130.3, 133.7, 134.7, 150.5, 152.0, 171.2; ESI-MS m/z 424.1 [M+H]$^+$; HRMS Calcd for C$_{20}$H$_{23}$NO$_5$SCl [M+H]$^+$ m/z 424.0989, found 424.0985.

Example 21

(S)-Methyl 2-(2-(benzyloxycarbonyloxy)-6,7-dihydrothieno[3,2-c]pyridin-5(4H)-yl)-2-(2-chlorophenyl)-acetate (I-17)

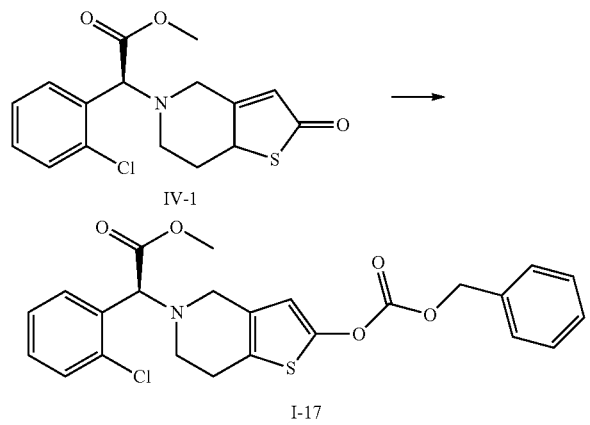

Following the method described in Example 18, (2S)-methyl 2-(2-chlorophenyl)-2-(2-oxo-7,7α-dihydrothieno[3,2-c]pyridin-5(2H,4H,6H)-yl)-acetate (IV-1) (85 mg) was reacted with benzyl chloroformate (0.25 ml), to prepare (S)-methyl 2-(2-(benzyloxycarbonyloxy)-6,7-dihydrothieno[3,2-c]pyridin-5(4H)-yl)-2-(2-chlorophenyl)-acetate (I-17) (97 mg). Yield 82%, ee=93.7% (chiral HPLC analysis conditions were the same as those in example 4), $[\alpha]_D^{20}$=+12.00° (c 0.50, CHCl$_3$); $^1$H-NMR (300 MHz, CDCl$_3$) δ 2.76-2.78 (m, 2H), 2.86-2.90 (m, 2H), 3.52 (d, 1H, J=14.4 Hz), 3.63 (d, 1H, J=14.4 Hz), 3.72 (s, 3H), 4.90 (s, 1H), 5.26 (s, 2H), 6.30 (s, 1H), 7.24-7.42 (m, 4H); $^{13}$C-NMR (75 MHz, CDCl$_3$) δ 25.1, 48.1, 50.3, 52.1, 67.8, 70.9, 112.5, 126.0, 127.0, 127.1, 128.6, 128.7, 128.9, 129.4, 129.5, 129.8, 129.9, 133.7, 134.3, 134.7, 150.4, 152.6, 171.2; ESI-MS m/z 472.1 [M+H]$^+$, 494.1 [M+Na]$^+$; HRMS Calcd for C$_{24}$H$_{23}$NO$_5$SCl [M+H]$^+$ m/z 472.0996, found 472.0985.

Example 22

(S)-Methyl 2-(2-(N,N-dimethylcarbamoyloxy)-6,7-dihydrothieno[3,2-c]pyridin-5(4H)-yl)-2-(2-chlorophenyl)-acetate (I-18)

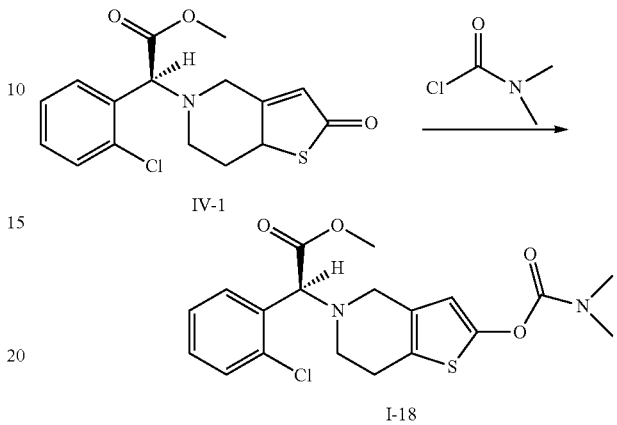

In an ice bath, sodium hydride (20 mg, 60%) were added to 6 ml of anhydrous N,N-dimethyl formamide, to which 169 mg of (2S)-methyl 2-(2-chlorophenyl)-2-(2-oxo-7,7a-dihydrothieno[3,2-c]pyridine-5(2H,4H,6H)-yl)-acetate (IV-1) was then added. The reaction was naturally warmed to room temperature, stirred for 1 hr, and then cooled to 0° C. 200 μl of N,N-dimethylcarbamoyl chloride was slowly added dropwise. The reaction was naturally warmed to room temperature, and stirred for 3 hrs, and at this time, TLC showed that the raw materials substantially disappeared. The reaction solution was poured into water (30 ml), the aqueous phase was extracted with ethyl acetate (50 ml×3), and the organic phase was dried to obtain a crude product, which was subjected to flash column chromatography (petroleum ether:ethyl acetate=40:3), to obtain (S)-methyl 2-(2-(N,N-dimethylcarbamoyloxy)-6,7-dihydrothieno[3,2-c]pyridin-5(4H)-yl)-2-(2-chlorophenyl)-acetate (I-18) (95 mg). Yield: 45%, mp 96-98° C., ee=93.5% (chiral HPLC analysis conditions were the same as those in Example 10), $[\alpha]_D^{20}$=+34° (c 0.50, MeOH); $^1$H-NMR (500 MHz, CDCl$_3$) δ 2.73-2.76 (m, 2H), 2.85-2.89 (m, 2H), 2.99 (s, 3H), 3.03 (s, 3H), 3.52 (d, 1H, J=14.3 Hz), 3.63 (d, 1H, J=14.3 Hz), 3.72 (s, 3H), 4.91 (s, 1H), 6.19 (s, 1H), 7.26-7.69 (m, 4H); $^{13}$C-NMR (75 MHz, CDCl$_3$) δ 25.03, 36.37, 36.88, 48.18, 50.40, 52.12, 67.87, 111.48, 125.38, 127.12, 129.09, 129.37, 129.76, 129.95, 130.56, 133.80, 134.34, 134.68, 151.04, 171.27; ESI-MS m/z 409.2 [M+H]$^+$; HRMS Calcd for C$_{19}$H$_{22}$N$_2$O$_4$SCl [M+H]$^+$ m/z 409.0992, found 409.0989.

Example 23

(S)-Methyl 2-(2-acetoxy-6,7-dihydrothieno[3,2-c]pyridin-5(4H)-yl)-2-(2-fluorophenyl)-acetate (I-19)

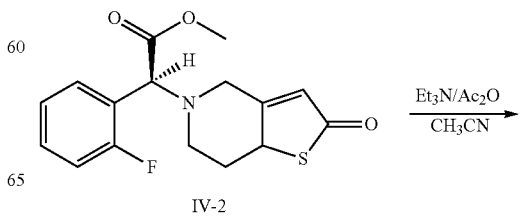

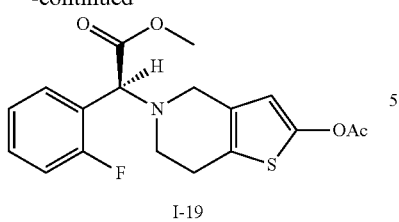

I-19

Following the method described in Example 4, (2S)-methyl 2-(2-fluorophenyl)-2-(2-oxo-7,7a-dihydrothieno[3.2-c]pyridin-5(2H,4H,6H)-yl)-acetate (IV-2) (100 mg) was reacted with acetic anhydride (63 µl), to prepare (S)-methyl 2-(2-acetoxy-6,7-dihydrothieno[3,2-c]pyridin-5(4H)-yl)-2-(2-fluorophenyl)-acetate (I-19) (98.0 mg). Yield 86%. $^1$H-NMR (300 MHz, CDCl$_3$) δ 2.26 (s, 3H), 2.47-2.97 (m, 4H), 3.64 (s, 2H), 3.74 (s, 3H), 4.80 (s, 1H), 6.27 (s, 1H), 7.07-7.59 (m, 4H); $^{13}$C-NMR (75 MHz, CDCl$_3$) δ 20.7, 24.9, 48.0, 50.0, 52.2, 64.3, 111.9, 115.5, 115.8, 124.4, 124.5, 125.6, 129.0, 130.0, 130.1, 130.2, 130.3, 149.6, 159.3, 162.6, 167.7, 171.0; ESI-MS m/z 364.1 [M+H]$^+$; HRMS Calcd for C$_{18}$H$_{19}$NO$_4$SF [M+H]$^+$ m/z 364.1019, found 364.1029.

Example 24

(S)-Methyl 2-(2-acetoxy-6,7-dihydrothieno[3,2-c]pyridin-5(4H)-yl)-2-(4-chlorophenyl)-acetate (I-20)

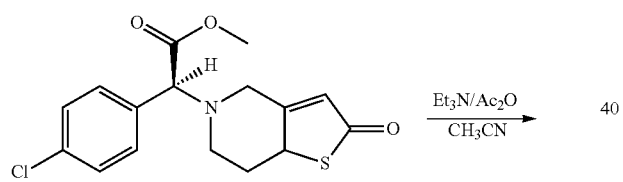

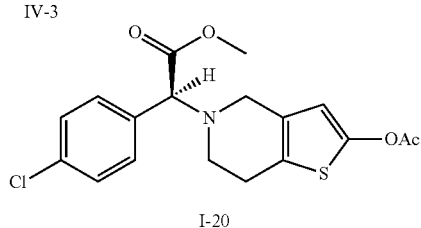

I-20

Following the method described in Example 4, (2S)-methyl 2-(4-chlorophenyl)-2-(2-oxo-7,7α-dihydrothieno[3,2-c]pyridin-5(2H,4H,6H)-yl)-acetate (IV-3) (100 mg) was reacted with acetic anhydride (63 µl), to prepare (S)-methyl 2-(2-acetoxy-6,7-dihydrothieno[3,2-c]pyridin-5(4H)-yl)-2-(4-chlorophenyl-acetate (I-20) (110 mg). Yield 97%. $^1$H-NMR (300 MHz, CDCl$_3$) δ 2.27 (s, 3H), 2.65-2.78 (m, 4H), 3.53 (s, 2H), 3.73 (s, 3H), 4.30 (s, 1H), 6.25 (s, 1H), 7.33-7.46 (m, 4H); $^{13}$C-NMR (75 MHz, CDCl$_3$) δ 20.7, 24.7, 48.1, 50.4, 52.2, 71.9, 111.9, 125.7, 128.9, 130.1, 134.3, 134.4, 149.6, 167.7, 171.4; ESI-MS m/z 380.1 [M+H]$^+$; HRMS Calcd for C$_{18}$H$_{19}$NO$_4$SCl [M+H]$^+$ m/z 380.0723, found 380.0735.

Example 25

(S)-Methyl 2-(2-acetoxy-6,7-dihydrothieno[3,2-c]pyridin-5(4H)-yl)-2-phenyl-acetate (I-21)

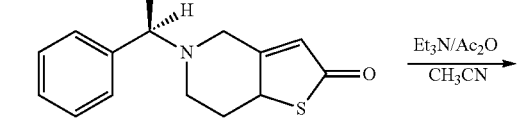

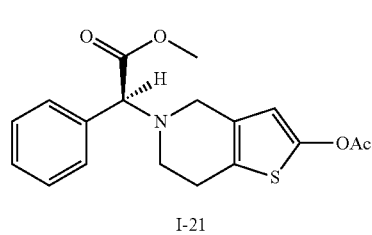

I-21

Following the method described in Example 4, (2S)-methyl 2-phenyl-2-(2-oxo-7,7α-dihydrothieno[3.2-c]pyridin-5(2H,4H,6H)-yl)-acetate (IV-4) (100 mg) was reacted with acetic anhydride (63 µl), to prepare (S)-methyl 2-(2-acetoxy-6,7-dihydrothieno[3,2-c]pyridin-5(4H)-yl)-2-phenyl-acetate (I-21) (108 mg). Yield 93%. $^1$H-NMR (300 MHz, CDCl$_3$) δ 2.26 (s, 3H), 2.47-2.91 (m, 4H), 3.54 (s, 2H), 3.72 (s, 3H), 4.32 (s, 1H), 6.25 (s, 1H), 7.25-7.69 (m, 5H); $^{13}$C-NMR (75 MHz, CDCl$_3$) δ 20.7, 24.4, 48.1, 50.3, 52.2, 72.5, 111.9, 128.7, 128.9, 167.7; ESI-MS m/z 346.1 [M+H]$^+$; HRMS Calcd for C$_{18}$H$_{20}$NO$_4$S [M+H]$^+$ m/z 346.1113, found 346.1125.

Example 26

(S)-Methyl 2-(2-(pyrrolidine-1-carbonyloxy)-6,7-dihydrothieno[3,2-c]pyridin-5(4H)-yl)-2-(2-chlorophenyl)-acetate (I-22)

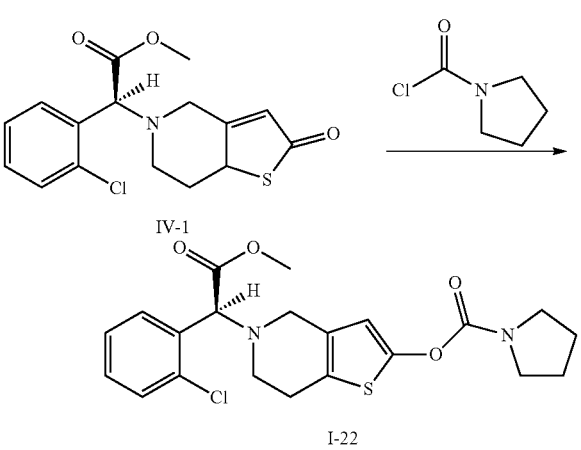

Following the method described in Example 22, (2S)-methyl 2-(2-chlorophenyl)-2-(2-oxo-7,7α-dihydrothieno[3,2-c]pyridin-5(2H,4H,6H)-yl)-acetate (IV-1) (84 mg) was reacted with pyrrolidine-1-carbonyl chloride (70 μl), to prepare (S)-methyl 2-(2-(pyrrolidine-1-carbonyloxy)-6,7-dihydrothieno[3,2-c]pyridin-5(4H)-yl)-2-(2-chlorophenyl)-acetate (I-22) (50 mg). Yield: 46%, ee=80.1% (chiral HPLC analysis conditions: Chiralpak IC 4.6 mm×250 mm; column temperature: 25° C.; mobile phase: 50% n-hexane/50% isopropanol/0.1% diethylamine; flow rate: 0.5 ml/min; detection wavelength: UV 254 rnn), $[\alpha]_D^{22}$=+19.0° (c 1.0, MeOH); $^1$H-NMR (300 MHz, CDCl$_3$) δ 1.87-2.04 (m, 4H), 2.62-2.75 (m, 2H), 2.77-2.89 (m, 2H), 3.44-3.54 (m, 5H), 3.61-3.76 (m, 4H), 4.89 (s, 1H), 6.20 (s, 1H), 7.22-7.40 (m, 4H); $^{13}$C-NMR (75 MHz, CDCl$_3$) δ 24.9, 25.1, 25.7, 29.7, 46.3, 46.6, 48.2, 50.4, 52.1, 67.9, 111.5, 125.2, 127.1, 128.6, 129.1, 129.3, 129.7, 130.0, 133.9, 134.7, 151.0, 151.8, 171.3; ESI-MS m/z 435.1 [M+H]$^+$; HRMS Calcd for C$_2$IH$_{24}$N$_2$O$_4$SCl [M+H]$^+$ m/z 435.1145, found 435.1148.

Example 27

(S)-Methyl 2-(2-(methoxycarbonyloxy)-6,7-dihydrothieno[3,2-c]pyridin-5(4H)-yl)-2-(2-chlorophenyl)-acetate (I-23)

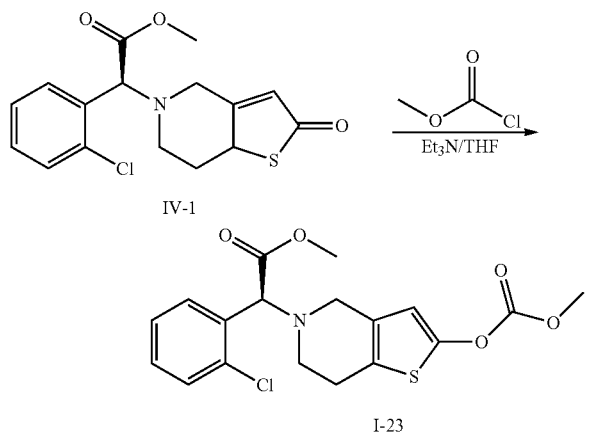

Following the method described in Example 18, (2S)-methyl 2-(2-chlorophenyl)-2-(2-oxo-7,7α-dihydrothieno[3.2-c]pyridin-5(2H,4H,6H)-yl)-acetate (IV-1) (108.5 mg) was reacted with 0.1 ml of methyl chloroformate, to prepare (S)-methyl 2-(2-(methoxycarbonyloxy)-6,7-dihydrothieno[3,2-c]pyridin-5(4H)-yl)-2-(2-chlorophenyl)-acetate (I-23) (86 mg). Yield: 68%, ee=97.0% (chiral HPLC analysis conditions were the same as those in Example 4), $[\alpha]_D^{20}$+24.00° (c 0.50, CHCl$_3$); $^1$H-NMR (300 MHz, CDCl$_3$) δ 2.75-2.78 (m, 2H), 2.83-2.90 (m, 2H), 3.47-3.68 (m, 2H), 3.72 (s, 3H), 3.90 (s, 3H), 4.90 (s, 1H), 6.29 (s, 1H), 7.23-7.68 (m, 4H); $^{13}$C-NMR (75 MHz, CDCl$_3$) δ 25.1, 48.1, 50.3, 52.1, 55.8, 67.8, 112.6, 126.0, 127.1, 129.4, 129.6, 129.8, 129.9, 133.7, 134.7, 150.4, 153.3, 171.2; ESI-MS m/z 396.1 [M+H]$^+$. HRMS Calcd for C$_{18}$H$_{19}$NO$_5$SCl [M+H]$^+$ m/z 396.0672, found 396.0675.

Example 28

(R,S)-Methyl 2-(2-(N,N-dimethylcarbamoyloxy)-6,7-dihydrothieno[3,2-c]pyridin-5(4H)-yl)-2-(2-chlorophenyl)-acetate (I-18')

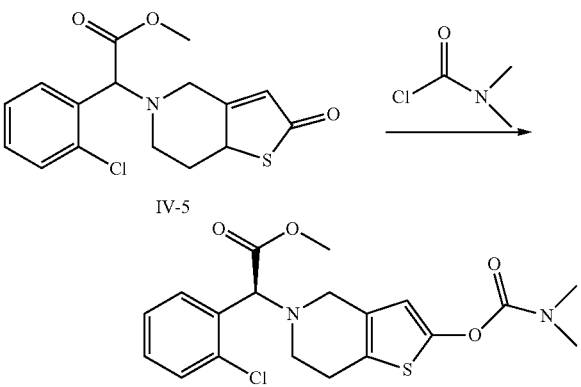

Following the method described in Example 22, methyl 2-(R,S)-2-(2-chlorophenyl)-2-(2-oxo-7,7α-dihydrothieno[3.2-c]pyridin-5(2H,4H,6H)-yl)-acetate (IV-5) (169 mg) was reacted with N,N-dimethylcarbamoyl chloride (200 μl), to prepare (R,S)-methyl 2-(2-(N,N-dimethylcarbamoyloxy)-6,7-dihydrothieno[3,2-c]pyridin-5(4H)-yl)-2-(2-chlorophenyl)-acetate (I-18') (185 mg). Yield: 87%. $^1$H-NMR (300 MHz, CDCl$_3$) δ 2.73-2.76 (m, 2H), 2.85-2.90 (m, 2H), 2.98 (s, 3H), 3.02 (s, 3H), 3.52 (d, 1H, J=14.3 Hz), 3.62 (d, 1H, J=14.3 Hz), 3.72 (s, 3H), 4.91 (s, 1H), 6.19 (s, 1H), 7.26-7.69 (m, 4H); ESI-MS m/z 409 [M+H]$^+$.

Example 29

(R,S)-Methyl 2-(2-acetoxy-6,7-dihydrothieno[3,2-c]pyridin-5(4H)-yl)-2-(2-chlorophenyl)-acetate (I-2")

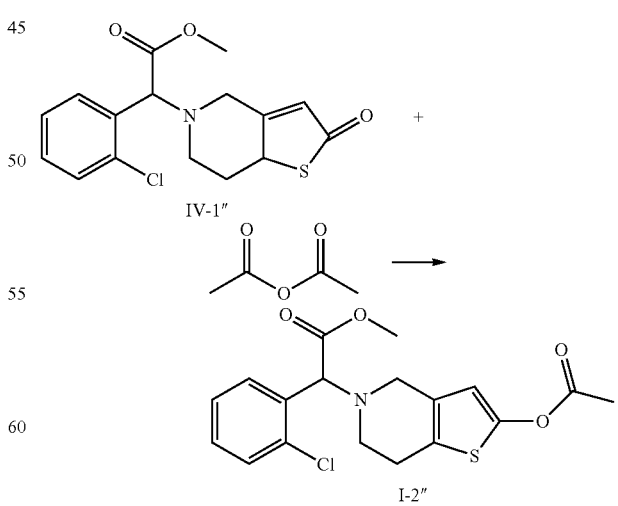

Following the method described in Example 4, methyl 2-(R,S)-2-(2-chlorophenyl-7,7α-dihydrothieno[3.2-c]pyridin-5(2H,4H,6H)-yl)-acetate (IV-1") (650 mg) was reacted with acetic anhydride (1 ml), to prepare (R,S)-methyl 2-(2-acetoxy-6,7-dihydrothieno[3,2-c]pyridin-5(4H)-yl)-2-(2-chlorophenyl)-acetate (I-2") (670 mg). Yield 92%. $^1$H-NMR (300 MHz, CDCl$_3$) δ 2.26 (s, 3H), 2.76 (d, 2H, J=5.4 Hz), 2.90 (d, 2H, J=5.0 Hz), 3.55 (d, 1H, J=14.2 Hz), 3.64 (d, 1H, J=14.2 Hz), 3.72 (s, 3H), 4.90 (s, 1H), 6.26 (s, 1H), 7.25-7.68 (m, 4H); ESI-MS m/z 380.0 [M+H]$^+$.

Example 30

(S)-Methyl 2-(2-acetoxy-6,7-dihydrothieno[3,2-c]pyridin-5(4H)-yl)-2-(2-chlorophenyl)-acetate Hydrochloride (I-2 Hydrochloride)

103 mg of (S)-methyl 2-(2-acetoxy-6,7-dihydrothieno[3,2-c]pyridin-5(4H)-yl)-2-(2-chlorophenyl)-acetate (I-2) was dissolved in 6 ml of diethyl ether, and stirred in an ice-salt bath at −10° C. A hydrogen chloride saturated ethanol solution (0.2 ml) was added slowly dropwise, till the system reached about pH 2, at which a white solid was precipitated immediately. It was stirred for 5 min, allowed to stand, quickly filtered under a nitrogen atmosphere, and washed with a suitable amount of diethyl ether. The resulting solid was dried in vacuum to obtain the I-2 hydrochloride (101 mg, white solid). Yield: 90%, and melting range: 100-120° C.

Example 31

(S)-methyl 2-(2-pivaloyloxy-6,7-dihydrothieno[3,2-c]pyridin-5(4H)-yl)-2-(2-chlorophenyl)-acetate Hydrochloride (I-7 Hydrochloride)

65 mg of (S)-methyl 2-(2-pivaloyloxy-6,7-dihydrothieno[3,2-c]pyridin-5(4H)-yl)-2-(2-chlorophenyl)-acetate (I-7) was dissolved in 4 ml of diethyl ether, and stirred in an ice-salt bath at −10° C. A hydrogen chloride saturated ethanol solution (0.2 ml) was added slowly dropwise, till the system reached about pH 2, at which a white solid was precipitated immediately. It was stirred for 5 min, allowed to stand, quickly filtered under a nitrogen atmosphere, and washed with a suitable amount of diethyl ether. The resulting solid was dried in vacuum to obtain the I-7 hydrochloride (65 mg, granular solid). Yield: 92%, melting point: 135-137° C.; $^1$H-NMR (300 MHz, CDCl$_3$) δ 1.33 (s, 9H), 3.08 (s, 2H), 3.44-3.51 (m, 2H), 3.82 (s, 4H), 4.34 (s, 1H), 5.59 (s, 1H), 6.39 (s, 1H), 7.44-7.50 (m, 3H), 8.36 (d, 1H, J=7.2 Hz).

Example 32

(S)-methyl 2-(2-(2,2-dimethylbutanoyloxy)-6,7-dihydrothieno[3,2-c]pyridin-5(4H)-yl)-2-(2-chlorophenyl)-acetate Hydrochloride (I-8 Hydrochloride)

63 mg of (S)-methyl 2-(2-(2,2-dimethylbutanoyloxy)-6,7-dihydrothieno[3,2-c]pyridin-5(4H)-yl)-2-(2-chlorophenyl)-acetate (I-8) was dissolved in 4 ml of diethyl ether, and stirred in an ice-salt bath at −10° C. A hydrogen chloride saturated ethanol solution (0.2 ml) was added slowly dropwise, till the system reached about pH 2, at which a white solid was precipitated immediately. It was stirred for 5 min, then allowed to stand, quickly filtered under a nitrogen atmosphere, and washed with a suitable amount of diethyl ether. The resulting solid was dried in vacuum to obtain the I-8 hydrochloride (60 mg, white granular solid). Yield: 88%, melting point: 133-135° C.; $^1$H-NMR (300 MHz, CDCl$_3$) δ 0.91 (t, 3H, J=7.6 Hz), 1.29 (s, 6H), 1.69 (q, 2H, J=7.4 Hz), 3.08 (s, 1H), 3.48 (m, 2H), 3.83 (s, 4H), 4.35 (s, 1H), 5.59 (s, 1H), 6.37 (s, 1H), 7.44-7.50 (m, 3H), 8.36 (d, 1H, J=6.84 Hz).

Example 33

Anti-Platelet Aggregation Activity Test

Agents and preparations: clopidogrel sulfate was used as a positive control. The positive control and the test compounds (prepared in the above examples) were formulated in 0.5% CMC-Na (carboxymethylcellulose sodium) into suspensions for administration to animals.

Animals: male SD rats, weighed about 250 g, and supplied by Shanghai Super-B&K Laboratory Animal Corp. Ltd. Animal certificate No.: 2008001605451, and license No.: SCXK (Hu); SCXK (Hu) 2008-0016.

Instruments: a centrifuge (80-2 bench top low-speed centrifuge), an automatic platelet aggregation tester (STELLEXLG-PAPER-I platelet coagulation/aggregation analyzer), and others.

Methods: the pharmacological activity test of the compounds of the present invention for platelet aggregation was performed following Born's turbidimetric method (Nature, 1962, 194(4832): 927). An agglomeration-promoting substance, adenosine diphosphate (ADP), was added to a platelet rich plasma (PRP), and stirred to allow platelets to aggregate. The aggregation of platelets resulted in the change of optical density, which could be detected by a spectrometer. This experiment can be used to evaluate the platelet aggregation effect induced by the test compounds administrated in-vivo or in-vitro.

Anti-platelet aggregation activity test: the male SD rates weighed about 250 g were given with clopidogrel sulfate and the test agents (homogeneous suspensions in 0.5% CMC-Na at a concentration of 1 mg/ml) by oral gavage at a dose of 10 mg/kg or 3 mg/kg, and the blank control was given with the same volume of 0.5% CMC-Na by oral gavage. After 2 hrs, blood samples were collected from eye sockets of the rats using 3.8% sodium citrate as anticoagulant at a ratio of whole blood to anticoagulant of 9:1, and centrifuged at 1000 rpm for 7 min to prepare a platelet rich plasma (PRP). The PRP was adjusted with a platelet poor plasma (PPP) to maintain the platelet counts at 2×10$^6$/ml. The PRP was taken into a test cup, and incubated at 37° C. for 10 min. Light transmission was adjusted to 0% with PRP and to 100% with PPP for each measurement. By using ADP (with a final concentration of 5 μM) as an inducer, the platelet aggregation percentages were measured through the turbidimetric method using a platelet aggregation tester, and statistically compared by t-test. The platelet aggregation inhibition was calculated by the equation: platelet aggregation inhibition (%)=[1−(aggregation percent in dosed tube/aggregation percent in control tube)]×100%.

Results: the platelet aggregation inhibition after oral administration of the test compounds to the rats is determined through the turbidimetric method, and some test results are shown in Table 1. The results show that most of the test compounds exhibit a more potent anti-platelet aggregation activity than clopidogrel, and the compounds of (S)-configuration (e.g. I-2', Example 5) exhibit a more potent platelet aggregation inhibition than the corresponding enantiomers of (R)-configuration (e.g. I-2', Example 6) and racemic mixtures (e.g. I-2", Example 29).

TABLE 1

Platelet aggregation inhibition after oral administration of test compounds to rats

| Test compounds | Dosage (mg/kg) | Animals (n) | Aggregation inhibition (%) |
|---|---|---|---|
| Blank control | — | 6 | — |
| Clopidogrel sulfate | 10 | 6 | 79.6 |
|  | 3 | 6 | 15.4 |
| I-1 (Example 4) | 3 | 6 | 41.1 |
| I-2 (Example 5) | 10 | 6 | 83.5 |
|  | 3 | 6 | 69.9 |
| I-2' (Example 6) | 10 | 6 | 55.3 |
|  | 3 | 6 | 27.1 |
| I-2" (Example 29) | 10 | 6 | 78.5 |
|  | 3 | 6 | 43.92 |
| I-3 (Example 7) | 3 | 6 | 38.4 |
| I-4 (Example 8) | 3 | 6 | 46.2 |
| I-5 (Example 9) | 3 | 6 | 55.1 |
| I-6 (Example 10) | 3 | 6 | 31.3 |
| I-7 (Example 11) | 3 | 6 | 41.9 |
| I-8 (Example 12) | 3 | 6 | 35.7 |
| I-9 (Example 13) | 3 | 6 | 30.3 |
| I-10 (Example 14) | 3 | 6 | 36.8 |
| I-11 (Example 15) | 3 | 6 | 13.6 |
| I-12 (Example 16) | 3 | 6 | 18.3 |
| I-13 (Example 17) | 3 | 6 | 10.1 |
| I-14 (Example 18) | 3 | 6 | 62.9 |
| I-15 (Example 19) | 3 | 6 | 45.3 |
| I-16 (Example 20) | 3 | 6 | 52.7 |
| I-18 (Example 22) | 3 | 6 | 48.2 |
| I-19 (Example 23) | 3 | 6 | 63.5 |
| I-20 (Example 24) | 3 | 6 | 17.6 |
| I-21 (Example 25) | 3 | 6 | 9.1 |
| I-22 (Example 26) | 3 | 6 | 20.3 |
| I-18' (Example 28) | 3 | 6 | 29.8 |

Example 34

Researches on Pharmacokinetics and Bioavailability of Compound I-2 in Rats

Research background: it is reported (Thromb Haemost, 2000, 84: 891; Drug Metab Rev 2005, 37 (Suppl 2): 99) that oxidative metabolism of clopidogrel in vivo by the liver P450 enzyme system first produces the metabolic intermediate (2S)-methyl 2-(2-oxo-7,7a-dihydrothieno[3,2-c]pyridin-5(2H,4H,6H)-yl)-2-(2-chlorophenyl)-acetate (thiolactone IV-1, see Example 3 for preparation thereof), and then Compound IV-1 is further rapidly metabolized into the pharmacologically active metabolite. Therefore, Compound IV-1 is useful as an indicator for the production of the active metabolite of clopidogrel (Drug Metab Disp 2002, 30: 1288).

Experimental purposes: (1) the plasma concentration-time curves of Compound I-2, clopidogrel, and metabolite IV-1 thereof after the rats are respectively given with Compound I-2 and clopidogrel by oral gavage are investigated, so as to estimate corresponding pharmacokinetic parameters, evaluate the pharmacokinetic characteristics of Compound I-2 and clopidogrel in rats, determine the conversion of Compound I-2 into the metabolite IV-1 and the conversion degree, and compare the respective conversion degrees of Compound I-2 and clopidogrel to the metabolite IV-1; and (2) the plasma concentration-time curves of Compound IV-1 after administration to the rats via intravenous injection are investigated, so as to estimate corresponding pharmacokinetic parameters, and evaluate the absolute bioavailability of the metabolite IV-1 produced through respective metabolism of Compound I-2 and clopidogrel in the rats.

Methods: male SD rats weighed 210-230 g were divided into 3 groups at random, Compound I-2 group, clopidogrel sulfate group, and Compound IV-1 group. The rats were fasted overnight, but allowed free access to water. After 10 h, (1) the Compound I-2 group was administrated with Compound I-2 by oral gavage in a volume of 8 ml/kg at a concentration of 1.14 mg/ml at a dose of 24 µmol/kg, and blood samples were collected from retro-orbital plexus in rats before dosing (0 h) and at 0.25, 0.5, 1, 2, 4, 6, 8, and 24 hrs post-dose; (2) the clopidogrel sulfate group was administrated with clopidogrel sulfate by oral gavage in a volume of 8 ml/kg at a concentration of 1.26 mg/ml at a dose of 24 µmol/kg, and blood samples were collected from retro-orbital plexus in rats before dosing (0 h) and at 0.25, 0.5, 1, 2, 4, 6, 8, and 24 hrs post-dose; and (3) the Compound IV-1 group was administrated with Compound IV-1 via intravenous injection in a volume of 5 ml/kg at a concentration of 0.54 mg/ml at a dose of 8 µmol/kg, and blood samples were collected from retro-orbital plexus in rats before dosing (0 h) and at 0.083, 0.167, 0.5, 1, 2, 4, 6, 8, and 24 hrs post-dose. Plasmas were isolated after treatment with an anticoagulant and a stabilizer, the plasma samples were processed, and the concentrations of Compound I-2, clopidogrel, and Compound IV-1 in plasmas were measured by LC-MS/MS. Chromatography and MS conditions are shown in Tables 2 and 3.

TABLE 2

Chromatography conditions for samples and internal standard (diazepam)

| Chromatography column | ACE 3.0*50 mm, 5 µm, C18, P/NO: ACE-121-0503 | | |
|---|---|---|---|
| mobile phase | Time (min) | Phase A: water + 0.1% formic acid | Phase B: acetonitrile + 0.1% formic acid |
|  | 0-0.5 | 75% | 25% |
|  | 0.5-1.5 | 75%→5% | 25%→95% |
|  | 1.5-3.0 | 5% | 95% |
|  | 3.0-3.2 | 5%→75% | 95%→25% |
|  | 3.2-4.0 | 75% | 25% |
| Injector Column | Flow rate 10° C. 35° C. | 0.5 ml/min | |
| Injection valve |  Total time | Position | |
|  | 2.0 | B | |
|  | 3.2 | A | |
| Retention time (min) | Compound I-2: 2.66 min; Clopidogrel: 2.70 min; Compound IV-1: 2.60 min; and diazepam: 2.50 min | | |

TABLE 3

| Sample | Compound IV-1 | Clopidogrel | Compound | Diazepam |
|---|---|---|---|---|
| Ion source | | ESI | | |
| Polarity | | Positive | | |
| Scan mode | | Q1, Q3, MRM | | |
| Nebulizer gas | | 40 psi | | |
| Heater gas | | 40 psi | | |
| Curtain gas | | 20 psi | | |
| Spray voltage | | 5000 V | | |
| Declustering | 56 V | 53 V | 60 v | 105 v |
| Collision gas | 36 ev | 23 ev | 23 ev | 42 ev |
| Temperature | | 500 | | |
| Ion pair m/z | 338.2/154.9 | 322.0/212.0 | 380.0/212.0 | 285.3/154.0 |

MS conditions for samples and internal standard (diazepam)

Results: the plasma concentration-time data after administration of the test agents to the SD rats are shown in Tables 4, 5, and 6 (note: NA is not available). The results show that (1) after 3 SD rats are dosed with 24 µmol/kg Compound I-2 by oral gavage, the Compound IV-1 generated by metabolism has a elimination half-life of $t_{1/2}$=2.19±1.68 h, an area $AUC_{0-t}$ under the plasma concentration-time curve of 197±124 µg·h/L, an area $AUC_{0-\infty}$, under the plasma concentration-time curve of 211±119 µg·h/L, a peak time of $T_{max}$=1.17±0.764 h, a peak concentration of $C_{max}$=67.2±42.3 µg/L, and an absolute bioavailability of 24.6%; (2) after 3 SD rats are dosed with 24 µmol/kg clopidogrel sulfate by oral gavage, the Compound IV-1 generated by metabolism has an elimination half-life of =2.48±0.466 h, an area $AUC_{0-t}$ under the plasma concentration-time curve of 29.0±11.5 µg·h/L, an area $AUC_{0-\infty}$, under the plasma concentration-time curve of 32.2±10.9 µg·h/L, a peak time of $T_{max}$=0.583±0.382 h, a peak concentration of $C_{max}$=6.93±3.36 µg/L, and an absolute bioavailability of 3.63%; and (3) after 3 SD rats are dosed with 8 µmol/kg Compound IV-1 via intravenous injection, the Compound IV-1 has an elimination half-life of $t_{1/2}$=1.06±0.364 h, an area $AUC_{0-t}$ under the plasma concentration-time curve of 266±37.6 µg·h/L, an area $AUC_{0-\infty}$ under the plasma concentration-time curve of 268±38.3 µg·h/L, a peak time of $T_{max}$=0.0830 h, and a peak concentration of $C_{max}$=671±128 µg/L.

TABLE 4

Concentration-time data (ng/ml) of Compound IV-1 in plasma after administration of Compound I-2 to SD rats by oral gavage

| Animal No. | Time (h) | | | | | | | | |
|---|---|---|---|---|---|---|---|---|---|
| | 0 | 0.25 | 0.5 | 1 | 2 | 4 | 6 | 8 | 24 |
| 1# | 0 | 35.5 | 53.0 | 65.4 | 115 | 32.4 | 8.59 | 5.74 | ND |
| 10# | NA | 19.4 | 29.2 | 34.7 | 19.6 | 11.8 | 4.25 | 1.56 | ND |
| 11# | NA | 22.5 | 51.9 | 37.7 | 16.6 | 12.6 | 18.9 | 6.12 | ND |
| Mean ± | — | 25.8 | 44.7 | 45.9 | 50.4 | 18.9 | 10.6 | 4.47 | — |
| SD | — | 8.54 | 13.4 | 16.9 | 56.0 | 11.7 | 7.53 | 2.53 | — |

TABLE 5

Concentration-time data (ng/ml) of Compound IV-1 in plasma after administration of clopidogrel sulfate to SD rats by oral gavage

| Animal No. | Time (h) | | | | | | | | |
|---|---|---|---|---|---|---|---|---|---|
| | 0 | 0.25 | 0.5 | 1 | 2 | 4 | 6 | 8 | 24 |
| 5# | 0 | 8.99 | 10.3 | 10.8 | 7.57 | 4.70 | 3.15 | 0.895 | ND |
| 12# | NA | 4.73 | 4.46 | 4.38 | 4.27 | 2.48 | 1.35 | 0.887 | ND |
| 13# | NA | 4.18 | 5.27 | 5.09 | 3.21 | 2.69 | 2.87 | 0.924 | ND |
| Mean ± | — | 5.97 | 6.68 | 6.76 | 5.02 | 3.29 | 2.46 | 0.902 | — |
| SD | — | 2.63 | 3.16 | 3.52 | 2.27 | 1.23 | 0.969 | 0.0195 | — |

TABLE 6

Concentration-time data (ng/ml) of Compound IV-1 in plasma after intravenous injection of Compound IV-1 to SD rats

| Animal No. | Time (h) | | | | | | | | |
|---|---|---|---|---|---|---|---|---|---|
| | 0 | 0.083 | 0.167 | 0.5 | 1 | 2 | 4 | 6 | 8 | 24 |
| 7# | 0 | 696 | 317 | 108 | 51.0 | 10.9 | 3.94 | 1.29 | ND | ND |
| 8# | 0 | 785 | 417 | 129 | 49.3 | 9.06 | 2.87 | 0.977 | ND | ND |
| 9# | 0 | 533 | 311 | 107 | 37.3 | 9.74 | 2.02 | 1.06 | ND | ND |
| Mean ± | 0 | 671 | 348 | 115 | 45.9 | 9.90 | 2.94 | 1.11 | — | — |
| SD | 0 | 128 | 59.5 | 12.4 | 7.47 | 0.930 | 0.962 | 0.162 | — | — |

The estimated pharmacokinetic parameters after the SD rats are dosed with the test agents are shown in Tables 7, 8, and 9. (Note: in Tables 7, 8, and 9, it is assumed that Compound I-2 or clopidogrel can be totally converted into Compound IV-1 in the calculation of clearance $CL_{tot}$ and apparent volume of distribution $V_z$ of Compound IV-1, and thus the dosage in the calculation formula is that of Compound I-2 or clopidogrel equivalent to Compound IV-1)

TABLE 7

Pharmacokinetic parameters of metabolite (Compound IV-1) after administration of Compound I-2 to SD rats by oral gavage

| Equivalent of 8.1 mg/kg | $C_{max}$ (μg/L) | $T_{max}$ (h) | $t_{1/2}$ (h) | $CL_{tot}$ (L/h/kg) | $V_2$ (L/kg) | $AUC_{0-t}$ (μg · h/L) | $AUC_{0-\infty}$ (μg · h/L) |
|---|---|---|---|---|---|---|---|
| 1# | 115 | 2.00 | 1.07 | 23.7 | 36.6 | 338 | 342 |
| 10# | 34.7 | 1.00 | 1.37 | 75.0 | 148 | 105 | 108 |
| 11# | 51.9 | 0.500 | 4.12 | 44.0 | 261 | 147 | 184 |
| Mean ± | 67.2 | 1.17 | 2.19 | 47.6 | 149 | 197 | 211 |
| SD | 42.3 | 0.764 | 1.68 | 25.8 | 112 | 124 | 119 |

TABLE 8

Pharmacokinetic parameters of metabolite (Compound IV-1) after administration of clopidogrel sulfate to SD rats by oral gavage

| Equivalent of 8.1 mg/kg | $C_{max}$ (μg/L) | $T_{max}$ (h) | $t_{1/2}$ (h) | $CL_{tot}$ (L/h/kg) | $V_2$ (L/kg) | $AUC_{0-t}$ (μg · h/L) | $AUC_{0-\infty}$ (μg · h/L) |
|---|---|---|---|---|---|---|---|
| 5# | 10.8 | 1.00 | 1.95 | 181 | 510 | 42.2 | 44.7 |
| 12# | 4.73 | 0.250 | 2.65 | 331 | 1267 | 21.1 | 24.5 |
| 13# | 5.27 | 0.500 | 2.83 | 294 | 1199 | 23.7 | 27.6 |
| Mean ± | 6.93 | 0.583 | 2.48 | 269 | 992 | 29.0 | 32.2 |
| SD | 3.36 | 0.382 | 0.466 | 77.9 | 419 | 11.5 | 10.9 |

TABLE 9

Pharmacokinetic parameters of Compound IV-1 after intravenous injection of Compound IV-1 to SD rats

| Compound 2.7 mg/kg | $C_{max}$ (μg/L) | $T_{max}$ (h) | $t_{1/2}$ (h) | $CL_{tot}$ (L/h/kg) | $V_2$ (L/kg) | $AUC_{0-t}$ (μg · h/L) | $AUC_{0-\infty}$ (μg · h/L) |
|---|---|---|---|---|---|---|---|
| 7# | 696 | 0.0830 | 1.30 | 10.0 | 18.8 | 266 | 269 |
| 8# | 785 | 0.0830 | 1.25 | 8.84 | 15.9 | 304 | 306 |
| 9# | 533 | 0.0830 | 0.643 | 11.8 | 10.9 | 229 | 229 |
| Mean ± | 671 | 0.0830 | 1.06 | 10.2 | 15.2 | 266 | 268 |
| SD | 128 | 0 | 0.364 | 1.49 | 3.98 | 37.6 | 38.3 |

Conclusions: (1) after being dosed to the rats by oral gavage, Compound I-2 can be converted into the main intermediate metabolite (Compound IV-1) of clopidogrel; and (2) by oral gavage, the degree of conversion of Compound I-2 into the metabolite IV-1 is more than 5 times higher than that of clopidogrel sulfate, and the absolute bioavailability of the metabolite IV-1 produced by metabolism of Compound I-2 is also more than 5 times higher than that of the metabolite IV-1 produced by metabolism of clopidogrel sulfate.

The above research results suggest that the bioavailability of the intermediate metabolite of Compound I-2 is significantly higher than that of clopidogrel, such that the production of the active metabolite thereof is also significantly higher than that of clopidogrel, and thus it is expected that the risk of side effects such as bleeding of the anti-platelet aggregation agent can be reduced while rapid onset of action and high efficacy are achieved, by significantly lowering the dosage of the agent.

Example 35

Tablet

Compound I-2 (50 g) prepared in Example 5, hydroxypropyl methylcellulose E (150 g), starch (200 g), a suitable amount of Povidone K30, and magnesium stearate (1 g) were mixed, granulated, and tableted.

What is claimed is:

1. A method for preparing an optically active 2-hydroxytetrahydro thienopyridine derivative, wherein said derivative is (S)-methyl 2-(2-acetoxy-6,7-dihydrothieno[3,2-c]pyridin-5(4H)-yl)-2-(2-chlorophenyl)-acetate of formula (I) or a pharmaceutically acceptable salt thereof, comprising the following steps:

(1) reacting an optically active compound of Formula II

II

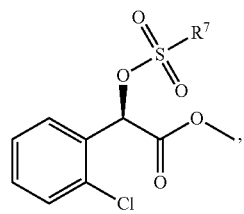

with a compound of Formula III

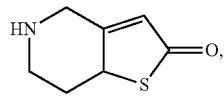
III or a salt thereof in the presence of a base, to obtain an optically active compound of Formula IV

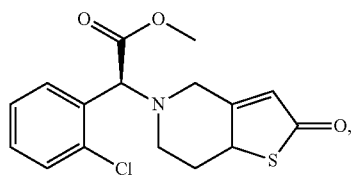
IV or a salt thereof, wherein $R^7$ is a $C_{1-6}$ alkyl, trifluoromethyl, pentafluoroethyl, heptafluoropropyl, phenyl, or a Z-substituted phenyl, in which Z is a $C_{1-3}$ alkyl, halo, cyano, nitro, or trifluoromethyl, and is at position 2, 3 or 4 of the phenyl ring; and (2) reacting the compound of Formula IV or the salt thereof with a compound of Formula V

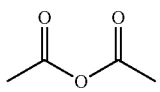

or a compound of Formula VI

in the presence of a base, to obtain the compound of Formula I,

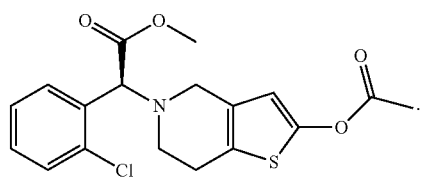
I

2. A method for preparing an optically active 2-hydroxytetrahydro thienopyridine derivative, wherein said derivative is (S)-methyl 2-(2-acetoxy-6,7-dihydrothieno[3,2-c]pyridin-5(4H)-yl)-2-(2-chlorophenyl)-acetate of formula (I) or a pharmaceutically acceptable salt thereof, comprising the following step:

reacting an optically active compound of Formula II

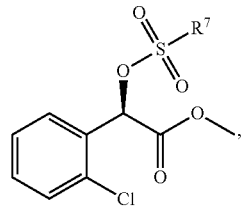
II with a compound of Formula VII

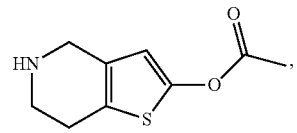
VII or a salt thereof in the presence of a base, to obtain the compound of Formula I,

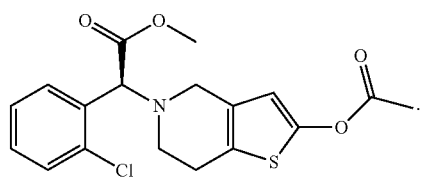
I wherein $R^7$ is a $C_{1-6}$ alkyl, trifluoromethyl, pentafluoroethyl, heptafluoropropyl, phenyl, or a Z-substituted phenyl, in which Z is a $C_{1-3}$ alkyl, halo, cyano, nitro, or trifluoromethyl, and is at position 2, 3 or 4 of the phenyl ring.

3. The method according to claim 1, wherein in the step (1), a reaction solvent is used and is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide; the base used is selected from triethylamine, diisopropyl ethylamine, 1,8-diazabicyclo[5,4,0]undec-7-ene, potassium carbonate, sodium carbonate, potassium bicarbonate, or sodium bicarbonate; the reaction temperature is from −20° C. to 100° C.; and the salt of the compound of Formula III is selected from hydrochloride, p-toluenesulfonate, acetate, sulfate, phosphate, trifluoromethane sulfonate, oxalate, methanesulfonate, benzenesulfonate, or hydrobromide; and wherein in the step (2), a reaction solvent is used and is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide; the base used is selected from triethylamine, sodium hydride, potassium hydride, 1,8-diazabicyclo[5,4,0]undec-7-ene, pyridine, diisopropylethylamine, lithium diisopropylamide, potassium carbonate, sodium carbonate, potassium bicarbonate, sodium bicarbonate, potassium t-butoxide, or sodium t-butoxide; and the reaction temperature is from −20° C. to 100° C.

4. The method according to claim 3, wherein in the step (1), said reaction solvent is one or more selected from N,N-dimethyl formamide, tetrahydrofuran, acetonitrile, or dichloromethane; and said reaction temperature is from 10° C. to 60° C.

5. The method according to claim 3, wherein in the step (2), said reaction solvent is one or more selected from tetrahydrofuran, acetonitrile, or N,N-dimethyl formamide; and said reaction temperature is from 0° C. to 50° C.

6. The method according to claim 2, wherein a reaction solvent is used and is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide; the base used is selected from triethylamine, diisopropyl ethylamine, 1,8-diazabicyclo[5,4,0]undec-7-ene, potassium carbonate, sodium carbonate, potassium bicarbonate, or sodium bicarbonate; the reaction temperature is from −20° C. to 100° C.; and the salt of the compound of Formula VII is selected from hydrochloride, p-toluenesulfonate, acetate, sulfate, phosphate, trifluoromethane sulfonate, oxalate, methanesulfonate, benzenesulfonate, or hydrobromide.

7. The method according to claim 6, wherein said solvent is one or more selected from N,N-dimethyl formamide, tetrahydrofuran, acetonitrile, or dichloromethane; and the reaction temperature is from 10° C. to 60° C.

8. A method for preparing an optically active 2-hydroxytetrahydro thienopyridine derivative, wherein said derivative is (S)-methyl 2-(2-acetoxy-6,7-dihydrothieno[3,2-c]pyridin-5(4H)-yl)-2-(2-chlorophenyl)-acetate of formula (I) or a pharmaceutically acceptable salt thereof, comprising the following step:

reacting the optically active compound of Formula IV

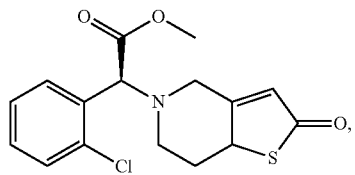

or the salt thereof with a compound of Formula V

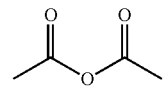

or a compound of Formula VI

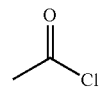

in the presence of a base, to obtain the compound of Formula I,

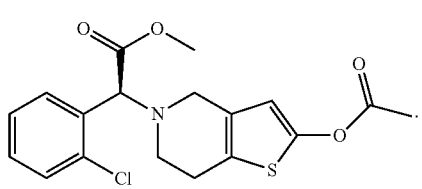

9. The method according to claim 8, wherein a reaction solvent is used and is one or more selected from benzene, toluene, chloroform, n-hexane, cyclohexane, dichloromethane, 1,2-dichloroethane, methyl t-butyl ether, carbon tetrachloride, ethyl acetate, propyl acetate, butyl acetate, methanol, ethanol, acetone, tetrahydrofuran, diethyl ether, acetonitrile, N,N-dimethyl formamide, or dimethyl sulfoxide; the base used is selected from triethylamine, sodium hydride, potassium hydride, 1,8-diazabicyclo[5,4,0]undec-7-ene, pyridine, diisopropylethylamine, lithium diisopropylamide, potassium carbonate, sodium carbonate, potassium bicarbonate, sodium bicarbonate, potassium t-butoxide, or sodium t-butoxide; and the reaction temperature is from −20° C. to 100° C.

* * * * *